US007410799B2

(12) United States Patent
Selden et al.

(10) Patent No.: US 7,410,799 B2
(45) Date of Patent: *Aug. 12, 2008

(54) IN VIVO PRODUCTION AND DELIVERY OF ERYTHROPOIETIN OR INSULINOTROPIN FOR GENE THERAPY

(75) Inventors: Richard F Selden, Wellesley, MA (US); Douglas Treco, Arlington, MA (US); Michael W. Heartlein, Boxborough, MA (US)

(73) Assignee: Shire Human Genetic Therapies, Inc., Cambridge, MA (US)

( * ) Notice: Subject to any disclaimer, the term of this patent is extended or adjusted under 35 U.S.C. 154(b) by 417 days.

This patent is subject to a terminal disclaimer.

(21) Appl. No.: 10/885,899

(22) Filed: Jul. 7, 2004

(65) Prior Publication Data

US 2005/0136041 A1   Jun. 23, 2005

Related U.S. Application Data

(63) Continuation of application No. 09/328,130, filed on Jun. 8, 1999, now Pat. No. 6,846,676, which is a continuation of application No. 08/334,455, filed on Nov. 4, 1994, now Pat. No. 5,994,127, which is a continuation of application No. 07/911,533, filed on Jul. 10, 1992, now abandoned, which is a continuation-in-part of application No. 07/787,840, filed on Nov. 5, 1991, now abandoned, and a continuation-in-part of application No. 07/789,188, filed on Nov. 5, 1991, now abandoned.

(51) Int. Cl.
*C12N 5/08* (2006.01)

(52) U.S. Cl. ............................. 435/366; 435/463

(58) Field of Classification Search ................. None
See application file for complete search history.

(56) References Cited

U.S. PATENT DOCUMENTS

| 4,396,601 A | 8/1983 | Salser et al. |
| 4,497,796 A | 2/1985 | Salser et al. |
| 4,789,550 A | 12/1988 | Hommel et al. |
| 4,892,538 A | 1/1990 | Aebischer et al. |
| 4,980,286 A | 12/1990 | Morgan et al. |
| 5,082,670 A | 1/1992 | Gage et al. |
| 5,089,397 A | 2/1992 | Kushner et al. |
| 5,166,059 A | 11/1992 | Pastan et al. |
| 5,175,255 A | 12/1992 | Thomason et al. |
| 5,194,596 A | 3/1993 | Tischer et al. |
| 5,219,740 A | 6/1993 | Miller et al. |
| 5,272,071 A | 12/1993 | Chappel |
| 5,399,346 A | 3/1995 | Anderson et al. |
| 5,441,868 A | 8/1995 | Lin |
| 5,460,959 A | 10/1995 | Mulligan et al. |
| 5,464,764 A | 11/1995 | Capecchi et al. |
| 5,578,461 A | 11/1996 | Sherwin et al. |
| 5,789,215 A | 8/1998 | Berns et al. |
| 5,994,127 A * | 11/1999 | Selden et al. ............... 435/325 |
| 6,048,524 A | 4/2000 | Selden et al. |
| 6,048,729 A | 4/2000 | Selden et al. |
| 6,054,288 A | 4/2000 | Selden et al. |
| 6,063,630 A | 5/2000 | Selden et al. |
| 6,846,676 B2 * | 1/2005 | Selden et al. ............... 435/455 |

FOREIGN PATENT DOCUMENTS

| EP | 0038765 | 3/1981 |
| EP | 0236059 | 9/1987 |
| EP | 0255231 | 2/1988 |
| EP | 0289034 | 11/1988 |
| EP | 0452894 | 10/1991 |
| GB | 2159172 | 11/1985 |
| WO | WO 87/00201 | 1/1987 |
| WO | WO 89/05345 | 12/1987 |
| WO | WO 88/00239 | 1/1988 |
| WO | WO 89/07136 | 2/1988 |
| WO | WO 88/08306 | 3/1988 |

(Continued)

OTHER PUBLICATIONS

Alberts, Molecular Biology of the Cell (Glossary), third edition, Garland Publishing, Inc., New York, 1994.
Antin et al., "Single Cell Analysis of Transfected Gene Expression in Primary Heart Cultures Containing Multiple Cell Types," BioTechniques 6:640-648, 1988.
Barr et al., "Systemic Delivery of Recombinant Proteins by Genetically Modified Myoblasts," Science 254:1507-1509, 1991.
Behr et al., "Efficient Gene Transfer Into Mammalian Primary Endocrine Cells with Lipopolyamine-coated DNA," Proceedings of the National Academy of Sciences U.S.A. 86:6982-6986, 1989.
Bennett et al., "A Role for Cyclosporin A in Gene Replacement Therapy," American Journal of Human Genetics 45:A109, 1989.
Bennett et al., "Suppression of Immunological Response Against a Novel Gene Product Delivered by Implants of Genetically Modified Fibroblasts," Molecular Biology and Medicine 7:471-477, 1990.

(Continued)

*Primary Examiner*—James S Ketter
(74) *Attorney, Agent, or Firm*—Clark & Elbing LLP

(57) ABSTRACT

The present invention relates to transfected primary and secondary somatic cells of vertebrate origin, particularly mammalian origin, transfected with exogenous genetic material (DNA) which encodes erythropoietin or an insulinotropin [e.g., derivatives of glucagon-like peptide 1 (GLP-1)], methods by which primary and secondary cells are transfected to include exogenous genetic material encoding erythropoietin or an insulinotropin, methods of producing clonal cell strains or heterogenous cell strains which express erythropoietin or an insulinotropin, methods of gene therapy in which the transfected primary or secondary cells are used, and methods of producing antibodies using the transfected primary or secondary cells. The present invention also includes primary and secondary somatic cells, such as fibroblasts, keratinocytes, epithelial cells, endothelial cells, glial cells, neural cells, formed elements of the blood, muscle cells, other somatic cells, which can be cultured and somatic cell precursors, which have been transfected with exogenous DNA encoding EPO or an insulinotropin, which is stably integrated into their genomes or is expressed in the cells episomally.

13 Claims, 7 Drawing Sheets

FOREIGN PATENT DOCUMENTS

| | | |
|---|---|---|
| WO | WO 89/01517 | 2/1989 |
| WO | WO 90/12878 | 5/1989 |
| WO | WO 90/15863 | 6/1989 |
| WO | WO 90/06757 | 6/1990 |
| WO | WO 90/11354 | 10/1990 |
| WO | WO 92/07573 | 10/1990 |
| WO | WO 92/12242 | 12/1990 |
| WO | WO 92/15676 | 3/1991 |
| WO | WO 91/06666 | 5/1991 |
| WO | WO 91/06667 | 5/1991 |
| WO | WO 91/09955 | 7/1991 |
| WO | WO 91/13151 | 9/1991 |
| WO | WO 91/19796 | 12/1991 |
| WO | WO 92/03917 | 3/1992 |
| WO | WO 92/08796 | 3/1992 |
| WO | WO 92/19255 | 11/1992 |
| WO | WO 92/20808 | 11/1992 |
| WO | WO 93/04169 | 3/1993 |
| WO | WO 90/06997 | 12/1998 |

OTHER PUBLICATIONS

Boggs, "Targeted Gene Modification for Gene Therapy of Stem Cells," International Journal of Cell Cloning 8:80-96, 1990.

Brash et al., "Strontium Phosphate Transfection of Human Cells in Primary Culture: Stable Expression of the Simian Virus 40 Large-T-Antigen Gene in Primary Human Bronchial Epithelial Cells," Molecular and Cellular Biology 7(5):2031-2034, 1987.

Brenner et al., "Expression of Collagen Genes in the Liver," Molecular Biology and Medicine 7:105-115, 1990.

Brigham et al., "Expression of a Prokaryotic Gene in Cultured Lung Endothelial Cells after Lipofection with a Plasmid Vector," Am. Journal of Respiratory Cell. and Molecular Biology 1:95-100, 1989.

Browne et al., "Erythropoietin: Gene Cloning, Protein Structure, and Biological Properties," Cold Spring Harbor Symposia on Quantitative Biology, vol. Ll, Cold Spring Harbor Laboratory Press, Cold Spring Harbor, New York, p. 693-702, 1986.

Burrin et al., "Regulation of Transfected Glycoprotein Hormone α-Gene Expression in Primary Pituitary Cell Cultures," Molecular Endocrinology 3(10):1643-1651, 1989.

Camerini-Otero, "Right on Target," The New Biologist 2:337-341, 1990.

Cann et al., "High Efficiency Transfection of Primary Human Lymphocytes and Studies of Gene Expression," Oncogene 3:123-128, 1988.

Capecchi, "High Efficiency Transformation by Direct Microinjection of DNA into Cultured Mammalian Cells," Cell 22:479-488, 1980.

Capecchi, "The New Mouse Genetics: Altering the Genome by Gene Targeting," Trends in Genetics 5:70-76, 1989.

Capecchi, "Altering the Genome by Homologous Recombination," Science 244:1288-1292, 1989.

Chang et al., "High Efficiency Gene Transfection by Electroporation Using a Radio-Frequency Electric Field," Biochimica et Biophysica Acta 1092:153-160, 1991.

Chang et al., "Autologous Fibroblast Implantation Feasibility and Potential Problems in Gene Replacement Therapy," Molecular Biology and Medicine 7:461-470, 1990.

Cline, "Perspectives for Gene Therapy: Inserting New Genetic Information into Mammalian Cells by Physical Techniques and Viral Vectors," Pharmacology and Therapy 29:69-92, 1985.

Corey et al., "Erythropoiesis in Murine Long-Term Marrow Cultures Following Transfer of the Erythropoietin cDNA into Marrow Stromal Cells," Experimental Hematology 18(3):201-204, 1990.

Crystal, "Transfer of Genes to Humans: Early Lessons and Obstacles to Success," Science 270:404-410, 1995.

Daubas et al., "Functional Activity of the Two Promoters of the Myosin Alkali Light Chain Gene in Primary Muscle Cell Cultures: Comparison with Other Muscle Gene Promoters and Other Culture Systems," Nucleic Acids Research 16(4):1251-1271, 1988.

Dhawan et al., "Systemic Delivery of Human Growth Hormone by Injection of Genetically Engineered Myoblasts," Science 254:1509-1512, 1991.

Diatloff-Zito et al., "Abnormal Response to DNA Crosslinking Agents of Fanconi Anemia Fibroblasts can be Corrected by Transfection with Normal Human DNA," Proceedings of the National Academy of Sciences U.S.A. 83:7034-7038, 1986.

Doering et al., "Expression of a Novel Gene Product by Transplants of Genetically Modified Primary Fibroblasts in the Central Nervous Systems," Journal of Neuroscience Research 29:292-298, 1991.

Doetschman et al., "Targeted Correction of a Mutant HPRT Gene in Mouse Embryonic Stem Cells," Nature 330:576-578, 1987.

Doetschman et al., "Targeted Mutation of the HPRT Gene in Mouse Embryonic Stem Cells," Proceedings of the National Academy of Sciences U.S.A. 85:8583-8587, 1988.

Drucker, et al., "Cell-Specific Post-Translational Processing of Preproglucagon Expressed from a Metallothionein-Glucagon Fusion Gene," The Journal of Biological Chemistry 261(21):9637-9643, 1986.

Duncan et al., Biochemistry (Moscow) 62:1263-1274, 1997.

Faulds et al., "Epoetin (Recombinant Human Erythropoietin) A Review of Its Pharmacodynamic and Pharmacokinetic Properties and Therapeutic Potential in Anaemia and the Stimulation of Erythropoiesis," Drugs 38(6):863-899, 1989.

Finn et al., "Homologous Plasmid Recombination is Elevated in Immortally Transformed Cells," Molecular and Cellular Biology 9:4009-4017, 1989.

Fishel et al., "Biochemical Studies of Homologous and Nonhomologous Recombination in Human Cells," Biochimie 73:257-267, 1991.

Fountain et al., "Transfection of Primary Human Skin Fibroblasts by Electroporation," Gene 68(1):167-172, 1988.

Friedmann, "Progress Toward Human Gene Therapy," Science 244:1275-1281, 1989.

Frohman, "Cut, Paste, and Save: New Approaches to Altering Specific Gene in Mice," Cell 56:145-147, 1989.

Gao et al., "A Novel Cationic Liposome Reagent for Efficient Transfection of Mammalian Cells," Biochemical and Biophysical Research Communications 179(1):280-285, 1995.

Gareis et al., "Homologous Recombination of Exogenous DNA Fragments with Genomic DNA in Somatic Cells of Mice," Cellular and Molecular Biology 37(2):191-203, 1991.

Ginot et al., "Transfection of Hepatic Genes into Adult Rat Hepatocytes in Primary Culture and their Tissue-Specific Expression," European Journal of Biochemistry 180:289-294, 1989.

Glover, "Expression of Cloned Genes in Animal Cells," In "Gene Cloning, The Mechanics of DNA Manipulation," pp. 179-202, Chapman and Hall, New York, 1984.

Hammer et al., "Partial Correction of Murine Hereditary Growth Disorder by Germ-Line Incorporation of a New Gene," Nature 311:65-67, 1984.

Harper et al., "Expression of Transfected DNA by Primary Murine Keratinocytes," Journal of Investigative Dermatology 91(2):150-153, 1988.

Heartlein et al., "Long-Term Production and Delivery of Human Growth Hormone," Proceedings of the National Academy of Sciences U.S.A. 91:10967-10971, 1994.

Hesse et al., "Regulated Gene Expression in Transfected Primary Chicken Erythrocytes," Proceedings of the National Academy of Sciences U.S.A. 83:4312-4316, 1986.

Iannuzzi et al., "The Introduction of Biologically Active Foreign Genes into Human Respiratory Epithelial Cells Using Electroporation," Am. Rev. of Resp. Dis. 138:965-968, 1988.

Imagawa et al., "Regulatory Elements of the Erythropoietin Gene," Blood 77(2):278-285, 1991.

Itzhaki et al., "Targeted Disruption of a Human Interferon-Inducible Gene Detected by Secretion of Human Growth Hormone," Nucleic Acids Research 19(4):3835-3842, 1991.

Jensen et al., "High-Frequency Transfection of Cultured Human Epidermal Basal Cells That Differentiate to Form a Multilayered Tissue," Experimental Cell Research 189:163-168, 1990.

Joyner et al., "Production of a Mutation in Mouse En-2 Gene by Homologous Recombination in Embryonic Stem Cells," Nature 338:153-155, 1989.

Kaufman et al., "Strategies for Obtaining High Level Expression in Mammalian Cells," Technique 2:221-236, 1990.

Keating et al., "Gene Transfer by Electroporation: A Model for Gene Therapy," Progress in Clinical Biological Research 333:491-498, 1990.

Keating et al., "Effect of Different Promoters on Expression of Genes Introduced Into Hematopoietic and Marrow Stromal Cells by Electroporation," Experimental Hematology 18:99-102, 1990.

Kendrew, The Encyclopedia of Molecular Biology, Blackwell Science Ltd., Oxford, p. 1085, 1994.

Kramerova et al., "Expression of the Cloned Human Erythropoietin Gene in CHO Cells," Biopolim Kletka 5(2):47-51, 1989.

Kremer et al., "Regulation of Parathyroid Hormone-like Peptide in Cultured Normal Human Keratinocytes," The Journal of Clinical Investigation 87:884-893, 1991.

Kriegler, "Gene Transfer and Expression: A Laboratory Manual," Stockton Press, New York, 1990.

Le Mouellic et al., "Targeted Replacement of the Homeobox Gene Hox-3.1 by the *Escherichia coli* lacZ in Mouse Chimeric Embryos," Proceedings of the National Academy of Sciences U.S.A. 87:4712-4716, 1990.

Ledley, "Clinical Considerations in the Design of Protocols for Somatic Gene Therapy," Human Gene Therapy 2:77-83, 1991.

Lee et al., "Glucagon Gene 3'-Flanking Sequences Direct Formation of Proglucagon Messenger RNA 3'-Ends in Islet and Nonislet Cells Lines," Molecular Endocrinology 4(6):800-806, 1990.

Lewin, Genes IV, Oxford Unversity Press, Oxford, p. 820, 1990.

Litwer et al., "Reversion of the Maple Syrup Urine Disease Phenotype of Impaired Branched Chain Alpha-Ketoacid Dehydrogenase Complex Activity in Fibroblasts from an Affected Child," The Journal of Biological Chemistry 264:14597-14600, 1989.

Loeffler et al., "Lipopolyamine-Mediated Transfection Allows Gene Expression Studies in Primary Neuronal Cells," Journal of Neurochemistry 54:1812-1815, 1990.

Lu et al., "Gene Transfer by Lipofection in Rabbit and Human Secretory Epithelial Cells," Pflügers Archives 415:198-203, 1989.

Lupton et al., "Dominant Positive and Negative Selection Using A Hygromycin Phosphotransferase-Thymidine Kinase Fusion Gene," Molecular and Cellular Biology 11(6):3374-3378, 1991.

Mansour, "Gene Targeting in Murine Embryonic Stem Cells: Introduction of Specific Alterations into the Mammalian Genome," Genet. Anal. Tech Appl. 7:219-227, 1990.

Mansour et al., "Disruption of the Proto-Oncogene int-2 in Mouse Embryo-Derived Stem Cells: A General Strategy for Targeting Mutations to Non-Selectable Genes," Nature 336:348-352, 1988.

Marshall, "Gene Therapy's Growing Pains," Science 269:1050-1055, 1995.

Mercola et al., "Insertion of New Genetic Information into Bone Marrow Cells of Mice: Comparison of Two Selectable Genes," Annals New York Academy of Sciences, p. 272-280, 1982.

Mes-Masson et al., "Expression of Oncomodulin does not Lead to the Transformation or Immortalization of Mammalian Cells In Vitro," Journal of Cellular Science 94:517-25, 1989.

Morgan et al., "Expression of an Exogenous Growth Hormone Gene by Transplantable Human Epidermal Cells," Science 237:1476-1479, 1987.

Morgenstern et al., "Advanced Mammalian Gene Transfer: High Titre Retroviral Vectors With Multiple Drug Selection Markers and a Complementary Helper-Free Packaging Cell Line," Nucleic Acids Research 18(12):3587-3596, 1990.

Narayanan et al., "In Vivo Expression of a Nonselected Gene Transferred into Murine Hematopoietic Stem Cells by Electroporation," Biochemical and Biophysical Research Communications 141:1018-1024, 1986.

Ogura et al., "Implantation of Genetically Manipulated Fibroblasts into Mice as Antitumor α-Interferon Therapy," Cancer Research 50:5102-5106, 1990.

Orkin et al., "Report and Recommendations of the Panel to Assess the NIH Investment in Research on Gene Therapy," 1995.

Osborne et al., "Design of Vectors for Efficient Expression of Human Purine Nucleoside Phosphorylase in Skin Fibroblasts from Enzyme-Deficient Humans," Proceedings of the National Academy of Sciences U.S.A. 85:6851-6855, 1988.

Palmer et al., "Genetically Modified Skin Fibroblast Persist Long After Transplantation but Gradually Inactivate Introduced Genes," Proceedings of the National Academy of Sciences U.S.A. 88:1330-1334, 1991.

Palmer et al., "Production of Human Factor IX in Animals by Genetically Modified Skin Fibroblasts: Potential Therapy for Hemophilia B," Blood 73:438-445, 1989.

Palmiter et al., "Metallothionein-Human GH Fusion Genes Stimulate Growth of Mice," Science 222:809-814, 1983.

Pasco et al., "Laboratory Methods, Efficient DNA-Mediated Gene Transfer into Primary Cultures of Adult Rat Hepatocytes," DNA 8(7):535-541, 1989.

Ponder et al., "Evaluation of Relative Promoter Strength in Primary Hepatocytes Using Optimized Lipofection," Human Gene Therapy 2:41-52, 1991.

Ponticelli et al., "Correction of Anaemia with Recombinant Human Erythropoietin," Nephron 52:201-208, 1989.

Potter, "Electroporation in Biology: Methods, Applications, and Instrumentation," Analytical Biochemistry 174:361-73, 1988.

Powell, "Human Erythropoietin Gene: High Level Expression in Stably Transfected Mammalian Cells and Chromosome Localization," Proceedings of the National Academy of Sciences U.S.A. 83:6465-6469, 1986.

Rippe et al., "DNA-Mediated Gene Transfer into Adult Rat Hepatocytes in Primary Culture," Molecular and Cellular Biology 10(2):689-695, 1990.

Robertson, "Using Embryonic Stem Cells to Introduce Mutations into the Mouse Germ Line," Biology of Reproduction 44:238-245, 1991.

Rodriguez et al., "Recombinant DNA Techniques: an Introduction," The Benjamin/Cummings Publishing Company, Inc., London, 1983.

Rosenfeld et al., "In Vivo Transfer of the Human Cystic Fibrosis Transmembrane Conductance Regulator Gene to the Airway Epithelium," Cell 68:143-155, 1992.

Sambrook et al., "Molecular Cloning," Cold Spring Harbor Laboratory Press, Cold Spring Harbor, New York, p. 16.3-16.4, 1989.

Sandhu et al., "Human Gene Therapy," Critical Reviews in Biotechnology 17:307-326, 1997.

Scharfmann et al., "Long-Term In Vivo Expression of Retrovirus-Mediated Gene Transfer in Mouse Fibroblast Implants," Proceedings of the National Academy of Sciences U.S.A. 88:4626-4630, 1991.

Sedivy et al., "Positive Genetic Selection for Gene Disruption in Mammalian Cells by Homologous Recombination," Proceedings of the National Academy of Sciences U.S.A. 86:227-231, 1989.

Selden et al., "Regulation of Insulin-Gene Expression," The New England Journal of Medicine 317:1067-1076, 1987.

Selden et al., "Implantation of Genetically Engineered Fibroblasts into Mice: Implications for Gene Therapy," Science 236:714-718, 1987.

Semenza et al., "Human Erythropoietin Gene Expression in Transgenic Mice: Multiple Transcription Initiation Sites and Cis-Acting Regulatory Elements," Molecular and Cellular Biology 10:930-938, 1990.

Shesely et al., "Correction of a Human $\beta^s$-globin Gene by Gene Targeting,"Proceedings of the National Academy of Sciences U.S.A. 88:4294-4298, 1991.

Sittler et al., "Tissue-Specific Expression of the Rat Growth Hormone Gene is Due to the Interaction of Multiple Promoter, Not Enhancer, Elements," DNA and Cell Biology 9(7):511-518, 1990.

Smith, "Regulation of Hematopoiesis," The Yale Journal of Biology and Medicine 63(5):371-380, 1990.

Spandidos, "Electric Field-Mediated Gene Transfer (Electroporation) into Mouse Friend and Human K562 Erythroleukemic Cells," Gene Anal. Tech. 4:50-56, 1987.

Stacey et al., "Electroporation and DNA-Dependent Cell Death in Murine Macrophages," Immunology and Cell Biology 71:75-85, 1993.

St. Louis et al., "An Alternative Approach to Somatic Cell Gene Therapy," Proceedings of the National Academy of Sciences U.S.A. 85:3150-3154, 1988.

Tatsuka et al., "An Improved Method of Electroporation for Introducing Biologically Active Foreign Genes Into Cultured Mammalian Cells," Experimental Cell Research 178:154-162, 1988.

Thomas et al., "Site-Directed Mutagenesis by Gene Targeting in Mouse Embryo-Derived Stem Cells," Cell 51:503-512, 1987.

Thomas et al., "Targeted Disruption of the Murine int-1 Proto-oncogene Resulting in Severe Abnormalities in Midbrain and Cerebellar Development," Nature 346:847-850, 1990.

Thompson et al., "Germ Line Transmission and Expression of a Corrected HPRT Gene Produced by Gene Targeting in Embryonic Stem Cells," Cell 56:313-321, 1989.

Toneguzzo et al., "Stable Expression of Selectable Genes Introduced into Human Hematopoietic Stem Cells by Electric Field-Mediated DNA Transfer," Proceedings of the National Academy of Sciences U.S.A. 83:3496-3499, 1986.

Treco et al., "Non-Viral Gene Therapy," Molecular Medicine Today 1:314-321, 1995.

Treco et al., "Fibroblast Cell Biology and Gene Therapy," Somatic Gene Therapy, ISBN 0-8493-2440-8:49-60, 1995.

Tur-Kaspa et al., "Use of Electroporation to Introduce Biologically Active Foreign Genes Into Primary Rat Hepatocytes," Molecular and Cellular Biology 6:716-718, 1986.

Vega, "Prospects for Homologous Recombination in Human Gene Therapy," Human Genetics 87:245-253, 1991.

Verma, "Gene Therapy," Scientific American, 68-84, Nov. 1990.

Verma et al., "Gene Therapy—Promises, Problems, and Prospects," Nature 389:239-242, 1997.

Vogelstein et al., "The Multistep Nature of Cancer," Trends in Genetics 9(4):138-141, 1993.

Weatherall, "Scope and Limitations of Gene Therapy," British Medical Bulletin 51:1-11, 1995.

Weidle et al., "A New Expression System for Mammalian Cells Based on Putative Replicator Sequences of the Mouse and Truncated Thymidine Kinase Gene," Gene 73:427-437, 1988.

Werner et al., "Expression of Transfected Genes by Differentiated, Postmitotic Neurons and Photoreceptors in Primary Cell Cultures," The Journal of Neuroscience Research 25:50-57, 1990.

Wolff et al., "Direct Gene Transfer into Mouse Muscle In Vivo," Science 247:1465-1468, 1990.

Wu, "Receptor-Mediated Gene Delivery In Vivo," The Journal of Biological Chemistry 266(22):14338-14342, 1991.

Yanagi et al., "Expression of Human Erythropoietin cDNA in Human Lymphoblastoid Namalwa Cells: the Inconsistency of Stable Expression Level with Transient Expression Efficiency," Gene 76:19-26, 1989.

Yang et al., "In Vivo and In Vitro Gene Transfer to Mammalian Somatic Cells by Particle Bombardment," Proceedings of the National Academy of Sciences U.S.A. 87:9568-9572, 1990.

Zheng et al. "Primary Cells and Established Cell Lines Join DNA Ends with the Same Efficiency Relative to Homologous Recombination," Plasmid 22:99-105, 1989.

Zheng et al., "Fidelity of Targeted Recombination in Human Fibroblasts and Murine Embryonic Stem Cells," Proceedings of the National Academy of Sciences 88:8067-8071, 1991.

\* cited by examiner

— 46.5kD

— 29.7

— 19.1

IN VIVO PRODUCTION AND DELIVERY OF ERYTHROPOIETIN OR INSULINOTROPIN FOR GENE THERAPY

CROSS REFERENCE TO RELATED APPLICATIONS

This application is a continuation of U.S. Ser. No. 09/328,130, filed Jun. 8, 1999 now U.S. Pat. No. 6,846,676, which is a continuation of U.S. Ser. No. 08/334,455, filed Nov. 4, 1994 (U.S. Pat. No. 5,994,127), which is a continuation of U.S. Ser. No. 07/911,533, filed Jul. 10, 1992 (abandoned), which is a continuation-in-part of U.S. Ser. No. 07/787,840, filed Nov. 5, 1991 (abandoned) and of U.S. Ser. No. 07/789,188, filed Nov. 5, 1991 (abandoned). The teachings of each of these prior applications are incorporated herein by reference.

BACKGROUND OF THE INVENTION

A variety of congenital, acquired, or induced syndromes are associated with insufficient numbers of erythrocytes (red blood cells or RBCs). The clinical consequence of such syndromes, collectively known as the anemias, is a decreased oxygen-carrying potential of the blood, resulting in fatigue, weakness, and failure-to-thrive. Erythropoietin (EPO), a glycoprotein of molecular mass 34,000 daltons, is synthesized and released into the systemic circulation in response to reduced oxygen tension in the blood. EPO, primarily synthesized in the kidney and, to a lesser extent, in the liver, acts on erythroid precursor cells [Colony Forming Units-Erythroid (CFU-E) and Burst-Forming Units-Erythroid (BFU-E)] to promote differentiation into reticulocytes and, ultimately, mature erythrocytes.

The kidney is the major site of EPO production and, thus, renal failure or nephrectomy can lead to decreased EPO synthesis, reduced RBC numbers, and, ultimately, severe anemia as observed in predialysis and dialysis patients. Subnormal RBC counts may also result from the toxic effects of chemotherapeutic agents or azidothymidine (AZT) (used in the treatment of cancers and AIDS, respectively) on erythroid precursor cells. In addition, a variety of acquired and congenital syndromes, such as aplastic anemia, myeloproliferative syndrome, malignant lymphomas, multiple myeloma, neonatal prematurity, sickle-cell anemia, porphyria cutanea tarda, and Gaucher's disease, include anemia as one clinical manifestation of the syndrome.

Purified human EPO or recombinant human EPO may be administered to patients in order to alleviate anemia by increasing erythrocyte production. Typically, the protein is administered by regular intravenous injections. The administration of EPO by injection is an imperfect treatment. Normal individuals maintain a relatively constant level of EPO, which is in the range of 6-30 mU/ml, depending on the assay used. After typical treatment regimens, serum EPO levels may reach 3,000-5,000 mU/Ml following a single injection, with levels falling over time as the protein is cleared from the blood.

If a relatively constant level of EPO is to be provided in the blood (i.e., to mimic the normal physiology of the protein), a delivery system that is capable of releasing a continuous, precisely dosed quantity of EPO into the blood is necessary.

SUMMARY OF THE INVENTION

The present invention relates to transfected primary and secondary somatic cells of vertebrate origin, particularly mammalian origin, transfected with exogenous genetic material (DNA or RNA), which encodes a clinically useful product, such as erythropoietin (EPO) or insulinotropin [e.g., derivatives of glucagon-like peptide 1 (GLP-1) such as GLP (7-37), GLP(7-36), GLP-1(7-35) and GLP-1(7-34) as well as their carboxyl-terminal amidated derivatives produced by in vivo amidating enzymes and derivatives which have amino acid alterations or other alterations which result in substantially the same biological activity or stability in the blood as that of a truncated GLP-1 or enhanced biological activity or stability], methods by which primary and secondary cells are transfected to include exogenous genetic material encoding EPO or insulinotropin, methods of producing clonal cell strains or heterogenous cell strains which express exogenous genetic material encoding EPO or insulinotropin, methods of providing EPO or insulinotropin in physiologically useful quantities to an individual in need thereof, through the use of transfected cells of the present invention or by direct injection of DNA encoding EPO into an individual; and methods of producing antibodies against the encoded product using the transfected primary or secondary cells. Transfected cells containing EPO-encoding exogenous genetic material express EPO and, thus, are useful for preventing or treating conditions in which EPO production and/or utilization are inadequate or compromised, such as in any condition or disease in which there is anemia. Similarly, transfected cells containing insulinotropin-encoding exogenous genetic material express insulinotropin and, thus, are useful for treating individuals in whom insulin secretion, sensitivity, or function is compromised (e.g., individuals with insulin-dependent or non-insulin dependent diabetes).

The present invention includes primary and secondary somatic cells, such as fibroblasts, keratinocytes, epithelial cells, endothelial cells, glial cells, neural cells, formed elements of the blood, muscle cells, and other somatic cells which can be cultured and somatic cell precursors, which have been transfected with exogenous DNA encoding EPO or exogenous DNA encoding insulinotropin. The exogenous DNA is stably integrated into the cell genome or is expressed in the cells episomally. The exogenous DNA encoding EPO is introduced into cells operatively linked with additional DNA sequences sufficient for expression of EPO in transfected cells. The exogenous DNA encoding EPO is preferably DNA encoding human EPO but, in some instances, can be DNA encoding mammalian EPO of non-human origin. EPO produced by the cells is secreted from the cells and, thus, made available for preventing or treating a condition or disease (e.g., anemia) in which EPO production and/or utilization is less than normal or inadequate for maintaining a suitable level of RBCs. Cells produced by the present method can be introduced into an animal, such as a human, in need of EPO and EPO produced in the cells is secreted into the systemic circulation. As a result, EPO is made available for prevention or treatment of a condition in which EPO production and/or utilization is less than normal or inadequate to maintain a suitable level of RBCs in the individual. Similarly, exogenous DNA encoding insulinotropin is introduced into cells operatively linked with additional DNA sequences sufficient for expression of insulinotropin in transfected cells. The encoded insulinotropin is made available to prevent or treat a condition in which insulin production or function is compromised or glucagon release from the pancreas is to be inhibited.

Primary and secondary cells transfected by the subject method can be seen to fall into three types or categories: 1) cells which do not, as obtained, produce and/or secrete the encoded protein (e.g., EPO or insulinotropin; 2) cells which produce and/or secrete the encoded protein (e.g., EPO or insulinotropin) but in lower quantities than normal (in quantities less than the physiologically normal lower level) or in defective form, and 3) cells which make the encoded protein (e.g., EPO or insulinotropin) at physiologically normal levels, but are to be augmented or enhanced in their production and/or secretion of the encoded protein.

Exogenous DNA encoding EPO is introduced into primary or secondary cells by a variety of techniques. For example, a construct which includes exogenous DNA encoding EPO and additional DNA sequences necessary for expression of EPO in recipient cells is introduced into primary or secondary cells by electroporation, microinjection, or other means (e.g., calcium phosphate precipitation, modified calcium phosphate precipitation, polybrene precipitation, microprojectile bombardment, liposome fusion, receptor-mediated DNA delivery). Alternatively, a vector, such as a retroviral vector, which includes exogenous DNA encoding EPO can be used, and cells can be genetically modified as a result of infection with the vector. Similarly, exogenous DNA encoding insulinotropin is introduced into primary or secondary cells using one of a variety of methods.

In addition to exogenous DNA encoding EPO or insulinotropin, transfected primary and secondary cells may optionally contain DNA encoding a selectable marker, which is expressed and confers upon recipient cells a selectable phenotype, such as antibiotic resistance, resistance to a cytotoxic agent, nutritional prototrophy or expression of a surface protein. Its presence makes it possible to identify and select cells containing the exogenous DNA. A variety of selectable marker genes can be used, such as neo, gpt, dhfr, ada, pac, hyg, mdr, and hisD.

Transfected cells of the present invention are useful, as populations of transfected primary cells, transfected clonal cell strains, transfected heterogenous cell strains, and as cell mixtures in which at least one representative cell of one of the three preceding categories of transfected cells is present, as a delivery system for treating an individual with a condition or disease which responds to delivery of EPO (e.g., anemia) or for preventing the development of such a condition or disease. In the methods of the present invention of providing EPO, transfected primary cells, clonal cell strains, or heterogenous cell strains are administered to an individual in need of EPO, in sufficient quantity and by an appropriate route, to deliver EPO to the systemic circulation at a physiologically relevant level. In a similar manner, transfected cells of the present invention providing insulinotropin are useful as populations of transfected primary cells, transfected clonal cell strains, transfected heterogenous cell strains, and as cell mixtures, as a delivery system for treating an individual in whom insulin production, secretion, or function is compromised or for inhibiting (totally or partially) glucagon secretion from the pancreas. A physiologically relevant level is one which either approximates the level at which the product is normally produced in the body or results in improvement of an abnormal or undesirable condition.

Clonal cell strains of transfected secondary cells (referred to as transfected clonal cell strains) expressing exogenous DNA encoding EPO (and, optionally, including a selectable marker gene) are produced by the method of the present invention. The present method includes the steps of: 1) providing a population of primary cells, obtained from the individual to whom the transfected primary cells will be administered or from another source; 2) introducing into the primary cells or into secondary cells derived from primary cells a DNA construct which includes exogenous DNA encoding EPO and additional DNA sequences necessary for expression of EPO, thus producing transfected primary or secondary cells; 3) maintaining transfected primary or secondary cells under conditions appropriate for their propagation; 4) identifying a transfected primary or secondary cell; and 5) producing a colony from the transfected primary or secondary cell identified in (4) by maintaining it under appropriate culture conditions and for sufficient time for its propagation, thereby producing a cell strain derived from the (founder) cell identified in (4). In one embodiment of the method, exogenous DNA encoding EPO is introduced into genomic DNA by homologous recombination between DNA sequences present in the DNA construct used to transfect the recipient cells and the recipient cell's genomic DNA. Clonal cell strains of transfected secondary cells expressing exogenous DNA encoding insulinotropin (and, optionally, including a selectable marker gene) are also produced by the present method.

In one embodiment of the present method of producing a clonal population of transfected secondary cells, a cell suspension containing primary or secondary cells is combined with exogenous DNA encoding EPO and DNA encoding a selectable marker, such as the bacterial neo gene. The two DNA sequences are present on the same DNA construct or on two separate DNA constructs. The resulting combination is subjected to electroporation, generally at 250-300 volts with a capacitance of 960 µFarads and an appropriate time constant (e.g., 14 to 20 msec) for cells to take up the DNA construct. In an alternative embodiment, microinjection is used to introduce the DNA construct containing EPO-encoding DNA into primary or secondary cells. In either embodiment, introduction of the exogenous DNA results in production of transfected primary or secondary cells. Using the same approach, electroporation or microinjection is used to produce a clonal population of transfected secondary cells containing exogenous DNA encoding insulinotropin alone, or insulinotropin and a selectable marker.

In the methods of producing heterogenous cell strains of the present invention, the same steps are carried out as described for production of a clonal cell strain, except that a single transfected primary or secondary cell is not isolated and used as the founder cell. Instead, two or more transfected primary or secondary cells are cultured to produce a heterogenous cell strain.

The subject invention also relates to methods of producing antibodies specific for EPO. In these methods, transfected primary or secondary cells expressing EPO are introduced into an animal recipient (e.g., rabbit, mouse, pig, dog, cat, goat, guinea pig, sheep, and non-human primate). The animal recipient produces antibodies against the EPO expressed, which may be the entire EPO protein antigen or a peptide encoded by a fragment of the intact EPO gene. Polyclonal sera is obtained from the animals. It is also possible to produce monoclonal antibodies through the use of transfected primary or secondary cells. Splenocytes are removed from an animal recipient of transfected primary or secondary cells expressing EPO. The splenocytes are fused with myeloma cells, using known methods, such as that of Koprowski et al. (U.S. Pat. No. 4,172,124) or Kohler et al. (Nature 256:495-497, 1975) to produce hybridoma cells which produce the desired anti-EPO monoclonal antibody. The polyclonal antisera and monoclonal antibodies produced can be used for the same purposes (e.g., diagnostic, preventive, or therapeutic purposes) as antibodies produced by other methods. Similarly, antibodies specific for insulinotropin can be produced by the methods of the present invention.

The present invention is particularly advantageous in treating anemia and other conditions in which EPO production, utilization, or both is compromised in that it: 1) makes it possible for one gene therapy treatment, when necessary, to last a patient's lifetime; 2) allows precise dosing (the patient's cells continuously determine and deliver the optimal dose of EPO based on physiologic demands, and the stably transfected cell strains can be characterized extensively in vitro prior to implantation, leading to accurate predictions of long term function in vivo); 3) is simple to apply in treating patients; 4) eliminates issues concerning patient compliance (periodic administration of EPO is no longer necessary); and 5) reduces treatment costs (since the therapeutic protein is synthesized by the patient's own cells, investment in costly protein production and purification facilities is unnecessary).

DETAILED DESCRIPTION OF THE INVENTION

Figure 1:
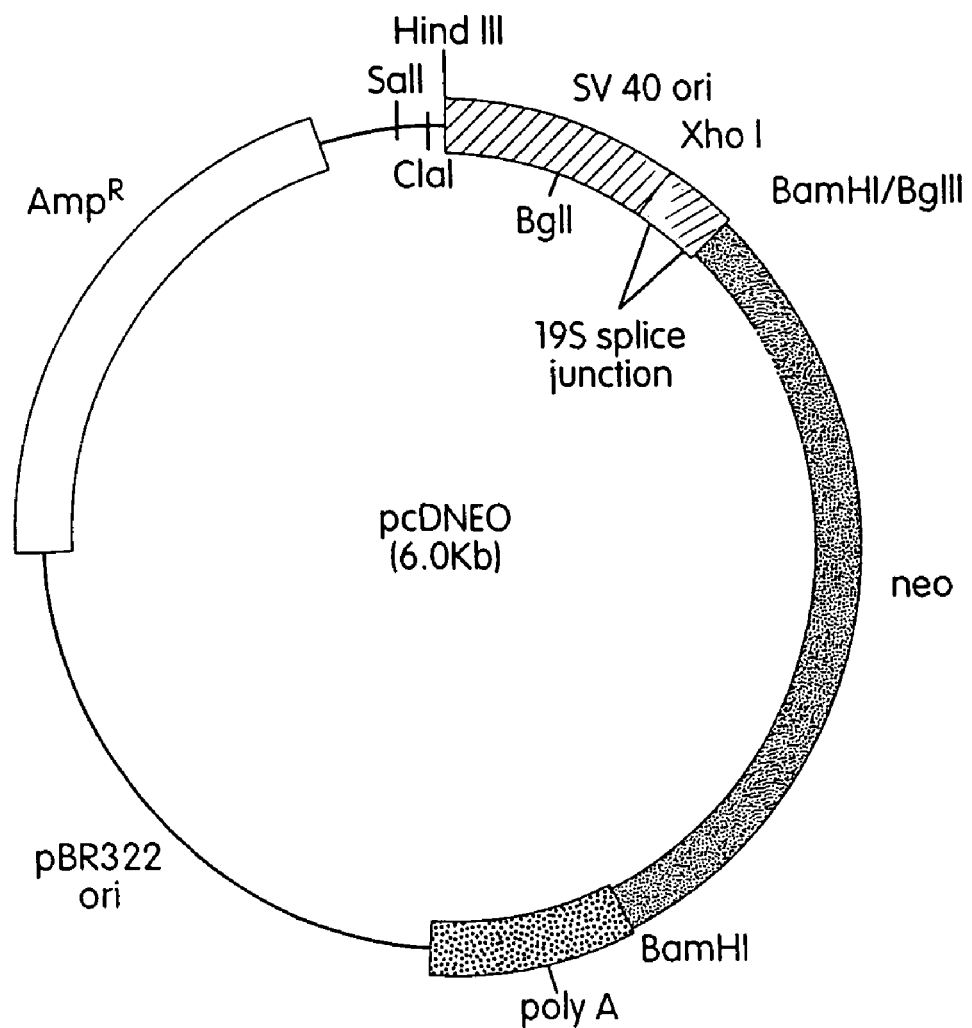
FIG. 1 is a schematic representation of plasmid pXEPO1. The solid black arc represents the pUC12 backbone and the arrow denotes the direction of transcription of the ampicillin resistance gene. The stippled arc represents the mouse metallothionein promoter (pmMT1). The unfilled arc interrupted by black boxes represents the human erythropoietin EPO gene (the black boxes denote exons and the arrow indicates the direction hEPO transcription). The relative positions of restriction endonuclease recognition sites are indicated.

The present invention relates to the use of genetically engineered cells to deliver a clinically useful or otherwise desirable substance to an individual in whom production of the substance is desired (e.g., to prevent or treat a disease or condition in which the product is produced or functions at an unacceptable level). In particular, it relates to the use of genetically engineered cells to deliver EPO to the systemic circulation of an individual in need of EPO, resulting in an increase in mature red blood cell numbers, an increase in the oxygen-carrying potential of the blood, and an alleviation of the symptoms of anemia. The present invention provides a means of delivering EPO at physiologically relevant levels and on a continuous basis to an individual. It further particularly relates to the use of genetically engineered cells to deliver insulinotropin to an individual in need of insulinotropin to stimulate insulin release, to increase insulin sensitivity in peripheral tissues, or to inhibit glucagon secretion from the pancreas.

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

As described herein, primary or secondary cells of vertebrate, particularly mammalian, origin have been transfected with exogenous DNA encoding EPO and shown to produce the encoded EPO reproducibly, both in vitro and in vivo, over extended periods of time. In addition, the transfected primary and secondary cells have been shown to express EPO in vivo at physiologically relevant levels. The EPO expressed has been shown to have the glycosylation pattern typical of EPO purified from human urine or recombinant human EPO. This demonstration is in sharp contrast to what one of skill in the art would predict, since, for example, even experts in the field see the finite life span of normal somatic cells and the inability to isolate or grow the relevant transplantable cells as precluding their use for gene therapy unless the cells are genetically modified using retroviruses (Miller, Blood, 76:271-278 (1990)). However, the transplantation of retrovirally treated fibroblasts has been shown to provide, at best, only transient metabolic improvements, and is seen to have serious limitations as a therapeutic system. In addition, until Applicants' work, this had not been done for EPO. Normal (nonimmortal) fibroblasts are characterized as being "much more difficult to transfect than continuous cell lines by using calcium phosphate precipitation techniques." (Miller, A. D., Blood, 76:271-278 (1990)). Furthermore, in considering non-retroviral techniques for gene therapy, it is typical of experts in the field to believe " . . . the efficiency of gene delivery is dismal . . . A physician would have to obtain an impossible number of cells from patients to guarantee the appropriate alteration of the millions required for therapy." (Verma, I. M., Scient. Amer., November 1990, pages 68-84).

Surprisingly, Applicants have been able to produce transfected primary and secondary cells which include exogenous DNA encoding EPO and express the exogenous DNA.

The transfected primary or secondary cells may also include DNA encoding a selectable marker which confers a selectable phenotype upon them, facilitating their identification and isolation. Applicants have also developed methods for producing transfected primary or secondary cells which stably express exogenous DNA encoding EPO, clonal cell strains and heterogenous cell strains of such transfected cells, methods of producing the clonal and heterogenous cell strains, and methods of using transfected cells expressing EPO to deliver the encoded product to an individual mammal at physiologically relevant levels. The constructs and methods are useful, for example, for treating an individual (human) whose EPO production and/or function is in need of being increased or enhanced [e.g., is compromised or less than normal, or normal but the individual would benefit from enhancement, at least temporarily, of red blood cell production (e.g., during predialysis or dialysis therapy, during treatment of AIDS with AZT, after surgery, or during chemotherapy)].

As also described herein, it is possible to transfect primary or secondary cells of vertebrate, particularly mammalian, origin with exogenous DNA encoding insulinotropin and to use them to provide insulinotropin to an individual in whom insulin production, function and/or sensitivity is compromised.

Transfected Cells

Primary and secondary cells to be transfected in order to produce EPO or insulinotropin can be obtained from a variety of tissues and include all cell types which can be maintained and propagated in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells, other somatic cells which can be cultured, and precursors of these somatic cell types. Primary cells are preferably obtained from the individual to whom the transfected primary or secondary cells are administered. However, primary cells may be obtained from a donor (other than the recipient) of the same species or another species (e.g., mouse, rat, rabbit, cat, dog, pig, cow, bird, sheep, goat, or horse).

Transfected primary and secondary cells can be produced, with or without phenotypic selection, as described herein, and shown to express exogenous DNA encoding EPO or exogenous DNA encoding insulinotropin.

Exogenous DNA

Exogenous DNA incorporated into primary or secondary cells by the present method is DNA encoding the desired product (e.g., EPO or insulinotropin), a functional or active portion, or a functional equivalent of EPO or insulinotropin (a protein which has a different amino acid sequence from that of EPO but has substantially the same biological function as EPO, or a protein which has a different amino acid sequence from that of GLP-1 related peptides but functions biologically as insulinotropin). The DNA can be obtained from a source in which it occurs in nature or can be produced, using genetic engineering techniques or synthetic processes. The DNA encoding EPO or insulinotropin will generally be DNA encoding the human product (i.e., human EPO or human insulinotropin). In some cases, however, the DNA can be DNA encoding EPO or insulinotropin of non-human origin (i.e., DNA obtained from a non-human source or DNA, produced recombinantly or by synthetic methods, which encodes a non-human EPO or insulinotropin).

The DNA transfected into primary or secondary cells can encode EPO alone or EPO and another product, such as a selectable marker to facilitate selection and identification of transfected cells. Alternatively, the transfected DNA can encode insulinotropin alone or insulinotropin and another product, such as a selectable marker. After transfection into primary or secondary cells, the exogenous DNA is stably incorporated into the recipient cell's genome (along with the additional sequences present in the DNA construct used), from which it is expressed or otherwise functions. Alternatively, the exogenous DNA may exist episomally within the transfected primary or secondary cells. DNA encoding the desired product can be introduced into cells under the control of an inducible promoter, with the result that cells produced or as introduced into an individual do not express the product but can be induced to do so (i.e., production is induced after the transfected cells are produced but before implantation or after implantation). DNA encoding the desired product can, of course, be introduced into cells in such a manner that it is expressed upon introduction (i.e., without induction).

Selectable Markers

A variety of selectable markers can be incorporated into primary or secondary cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac, hyg, and hisD. The selectable phenotype conferred makes it possible to identify and isolate recipient primary or secondary cells.

DNA Constructs

DNA constructs, which include exogenous DNA encoding the desired product (e.g., EPO, insulinotropin) and, optionally, DNA encoding a selectable marker, along with additional sequences necessary for expression of the exogenous DNA in recipient primary or secondary cells, are used to transfect primary or secondary cells in which the protein (e.g., EPO, insulinotropin) is to be produced. Alternatively, infectious vectors, such as retroviral, herpes, adenovirus, adenovirus-associated, mumps, and poliovirus vectors, can be used for this purpose.

Figure 4:
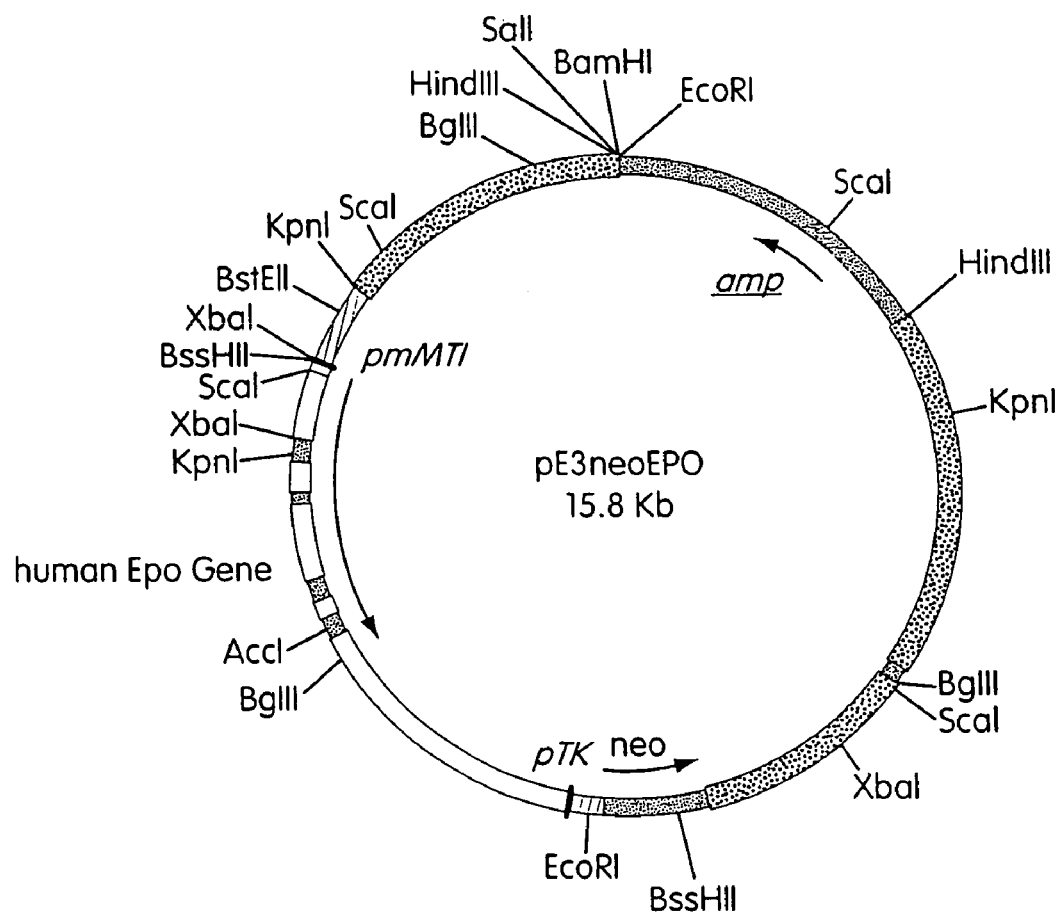
FIG. 4 is a schematic representation of plasmid pE3neoEPO. The positions of the human erythropoietin gene and the neo and amp resistance genes are indicated. Arrows indicate the directions of transcription of the various genes. pmMT1 denotes the mouse metallothionein promoter (driving hEPO expression) and pTK denotes the Herpes Simplex Virus thymidine kinase promoter (driving neo expression). The dotted regions of the map mark the positions of human HGPRT sequences. The relative positions of restriction endonuclease recognition sites are indicated.

A DNA construct which includes the exogenous DNA encoding EPO and additional sequences, such as sequences necessary for expression of EPO, can be used (e.g., plasmid pXEPO1; see FIG. 1). A DNA construct can include an inducible promoter which controls expression of the exogenous DNA, making inducible expression possible. Optionally, the DNA construct may include a bacterial origin of replication and bacterial antibiotic resistance markers, which allow for large-scale plasmid propagation in bacteria. A DNA construct which includes DNA encoding a selectable marker, along with additional sequences, such as a promoter, polyadenylation site, and splice junctions, can be used to confer a selectable phenotype upon transfected primary or secondary cells (e.g., plasmid pcDNEO). The two DNA constructs are cotransfected into primary or secondary cells, using methods described herein. Alternatively, one DNA construct which includes exogenous DNA encoding EPO, a selectable marker gene and additional sequences (e.g., those necessary for expression of the exogenous DNA and for expression of the selectable marker gene) can be used. Such a DNA construct (pE3neoEPO) is described in FIG. 4; it includes the EPO gene and the neo gene. Similar constructs, which include exogenous DNA encoding insulinotropin and additional sequences (e.g., sequences necessary for insulinotropin expression) can be produced (e.g., plasmid pXGLP1; see Example 11). These constructs can also include DNA encoding a selectable marker, as well as other sequences, such as a promoter, a polyadenylation site, and splice junctions.

In those instances in which DNA is injected directly into an individual, such as by injection into muscles, the DNA construct includes the exogenous DNA and regulatory sequences necessary and sufficient for expression of the encoded product (e.g., EPO) upon entry of the DNA construct into recipient cells.

Transfection of Primary or Secondary Cells and Production of Clonal or Heterogenous Cell Strains Transfection of cells by the present method is carried out as follows: vertebrate tissue is first obtained; this is carried out using known procedures, such as punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explantation. If enzymatic digestion is used, enzymes such as collagenase, hyaluronidase, dispase, pronase, trypsin, elastase, and chymotrypsin can be used.

Figure 2:
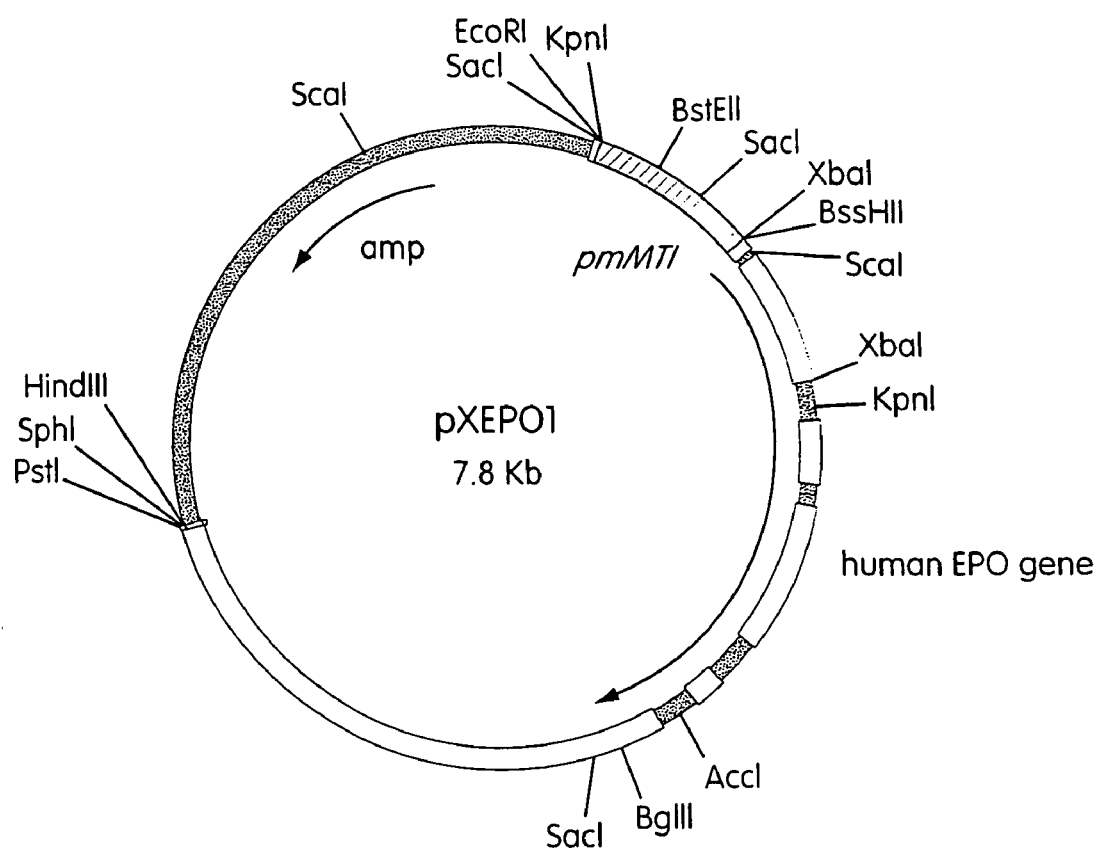
FIG. 2 is a schematic representation of plasmid pcDNEO. This plasmid has the neo gene from plasmid pSV2neo (a BamHI-BglII fragment) inserted into the BamHI site of plasmid pcD; the amp and pBR322ori sequences are from pBR322; the polyA, 19S splice junction, and early promoter sequences are from SV40.

The resulting primary cell mixture can be transfected directly, or it can be cultured first, removed from the culture plate, and resuspended before transfection is carried out. Primary cells or secondary cells are combined with exogenous DNA encoding EPO, to be stably integrated into their genomes and, optionally, DNA encoding a selectable marker, and treated in order to accomplish transfection. The exogenous DNA and selectable marker-encoding DNA can each be present on a separate construct (e.g., pXEPO1 and pcD-NEO, see FIGS. 1 and 2) or on a single construct (e.g., pE3neoEPO, see FIG. 4). An appropriate quantity of DNA to ensure that at least one stably transfected cell containing and appropriately expressing exogenous DNA is produced. In general, 0.1 to 500 µg DNA is used.

In one embodiment of the present method of producing transfected primary or secondary cells, transfection is effected by electroporation, as described in the Examples. Electroporation is carried out at appropriate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. As described herein, electroporation is very efficient if carried out at an electroporation voltage in the range of 250-300 volts and a capacitance of 960 µFarads (see Examples 4, 5, 7, and 8). Total DNA of approximately 0.1 to 500 µg is generally used. As described in the Examples, total DNA of 60 µg and voltage of 250-300 volts with capacitance of 960 µFarads for a time constant 14-20 of msec has been used and shown to be efficient.

In another embodiment of the present method, primary or secondary cells are transfected using microinjection. See, for instance, Examples 4 and 9. Alternatively, known methods such as calcium phosphate precipitation, modified calcium phosphate precipitation, polybrene precipitation, liposome fusion, and receptor-mediated gene delivery can be used to transfect cells. A stably, transfected cell is isolated and cultured and subcultivated, under culturing conditions and for sufficient time, to propagate the stably transfected secondary cells and produce a clonal cell strain of transfected secondary cells. Alternatively, more than one transfected cell is cultured and subculturated, resulting in production of a heterogenous cell strain.

Transfected primary or secondary cells undergo a sufficient number of doublings to produce either a clonal cell strain or a heterogenous cell strain of sufficient size to provide EPO to an individual in effective amounts. In general, for example, 0.1 cm$^2$ of skin is biopsied and assumed to contain 100,000 cells; one cell is used to produce a clonal cell strain and undergoes approximately 27 doublings to produce 100 million transfected secondary cells. If a heterogenous cell strain is to be produced from an original transfected population of approximately 100,000 cells, only 10 doublings are needed to produce 100 million transfected cells.

The number of required cells in a transfected clonal or heterogenous cell strain is variable and depends on a variety of factors, which include but are not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. To put these factors in perspective, to deliver therapeutic levels of EPO in an otherwise healthy 60 kg patient with anemia, the number of cells needed is approximately the volume of cells present on the very tip of the patient's thumb.

Episomal Expression of Exogenous DNA

DNA sequences that are present within the cell, yet do not integrate into the genome, are referred to as episomes. Recombinant episomes may be useful in at least three settings: 1) if a given cell type is incapable of stably integrating the exogenous DNA; 2) if a given cell type is adversely affected by the integration of DNA; and 3) if a given cell type is capable of improved therapeutic function with an episomal rather than integrated DNA.

Using the transfection and culturing approaches to gene therapy described in Examples 1 and 2, exogenous DNA encoding EPO, in the form of episomes can be introduced into vertebrate primary and secondary cells. Plasmid pE3neoEPO can be converted into such an episome by the addition of DNA sequences for the Epstein-Barr virus origin of replication and nuclear antigen [Yates, J. L., Nature 319:780-7883 (1985)]. Alternatively, vertebrate autonomously replicating sequences can be introduced into the construct (Weidle, U. H., Gene 73(2):427-437 (1988). These and other episomally derived sequences can also be included in DNA constructs without selectable markers, such as pXEPO1. The episomal exogenous DNA is then introduced into primary or secondary vertebrate cells as described in this application (if a selective marker is included in the episome, a selective agent is used to treat the transfected cells). Similarly, episomal expression of DNA encoding insulinotropin can be accomplished in vertebrate primary or secondary cells, using the same approach described above with reference to EPO.

Implantation of Clonal Cell Strain or Heterogenous Cell Strain of Transfected Secondary Cells The transfected cells produced as described above are introduced into an individual to whom EPO is to be delivered, using known methods. The clonal cell strain or heterogenous cell strain is introduced into an individual, using known methods, using various routes of administration and at various sites (e.g., renal subcapsular, subcutaneous, central nervous system (including intrathecal), intravascular, intrahepatic, intrasplanchnic, intraperitoneal (including intraomental), or intramuscular implantation)]. Once implanted in the individual, the transfected cells produce EPO encoded by the exogenous DNA. For example, an individual who has been diagnosed as anemic is a candidate for a gene therapy cure. The patient has a small skin biopsy performed; this is a simple procedure which can be performed on an out-patient basis. The piece of skin, approximately 0.1 cm$^2$, is taken, for example, from under the arm and requires about one minute to remove. The sample is processed, resulting in isolation of the patient's cells (in this case, fibroblasts) and genetically engineered to produce EPO. Based on the age, weight, and clinical condition of the patient, the required number of cells is grown in large-scale culture. The entire process usually requires 4-6 weeks and, at the end of that time, the appropriate number of genetically-engineered cells is introduced into the individual (e.g., by injecting them back under the patient's skin). The patient is now capable of producing his or her own EPO or additional EPO.

Transfected cells, produced as described above, which contain insulinotropin-encoding DNA are delivered into an individual in whom insulin production, secretion, function, and/or sensitivity is compromised. They are introduced into the individual by known methods and at various sites of administration (e.g., renal, subcapsular, subcutaneous, central nervous system (including intrathecal), intravascular, intrahepatic, intrasplanchnic, intraperitoneal (including intraomental) or intramuscular implantation). Once implanted in the individual, the transfected cells produce insulinotropin encoded by the exogenous DNA. For example, an individual in whom insulin production, secretion or sensitivity is impaired can receive therapy or preventive treatment through the implantation of transfected cells expressing exogenous DNA encoding insulinotropin produced as described herein. The cells to be genetically engineered are obtained as described above for EPO, processed in a similar manner to produce sufficient numbers of cells, and introduced back into the individual.

As this example suggests, the cells used will generally be patient-specific, genetically-engineered cells. It is possible, however, to obtain cells from another individual of the same species or from a different species. Use of such cells might require administration of an immunosuppressant, alteration of histocompatibility antigens, or use of a barrier device to prevent rejection of the implanted cells.

In one embodiment, a barrier device is used to prevent rejection of implanted cells obtained from a source other than the recipient (e.g., from another human or from a non-human mammal such as a cow, dog, pig, goat, sheep, or rodent). In this embodiment, transfected cells of the present invention are placed within the barrier device, which is made of a material (e.g., a membrane such as Amicon XM-50) which permits the product encoded by the exogenous DNA to pass into the recipient's circulation or tissues but prevents contact between the cells and the recipient's immune system and thus prevents an immune response to (and possible rejection of) the cells by the recipient. Alternatively, DNA encoding EPO or insulinotropin can be introduced into an individual by direct injection, such as into muscle or other appropriate site. In this embodiment, the DNA construct includes exogenous DNA encoding the therapeutic product (e.g., EPO, insulinotropin) and sufficient regulatory sequences for expression of the exogenous DNA in recipient cells. After injection into the individual, the DNA construct is taken up by some of the recipient cells. The DNA can be injected alone or in a formulation which includes a physiologically compatible carrier (e.g., a physiological buffer) and, optionally, other components, such as agents which allow more efficient entry of the DNA construct into cells, stabilize the DNA or protect the DNA from degradation.

Uses of Transfected Primary and Secondary Cells and Cell Strains

Transfected primary or secondary cells or cell strains have wide applicability as a vehicle or delivery system for EPO. The transfected primary or secondary cells of the present invention can be used to administer EPO, which is presently administered by intravenous injection. When transfected primary or secondary cells are used, there is no need for extensive purification of the polypeptide before it is administered to an individual, as is generally necessary with an isolated polypeptide. In addition, transfected primary or secondary cells of the present invention produce the therapeutic product as it would normally be produced.

An advantage to the use of transfected primary or secondary cells of the present invention is that by controlling the number of cells introduced into an individual, one can control the amount of EPO. In addition, in some cases, it is possible to remove the transfected cells if there is no longer a need for the product. A further advantage of treatment by use of transfected primary or secondary cells of the present invention is that production can be regulated, such as through the administration of zinc, steroids, or an agent which affects transcription of the EPO-encoding DNA.

Glucagon-like peptide 1 (GLP-1) and glucagon-like peptide 1 derivatives (GLP-1 derivatives) are additional molecules that can be delivered therapeutically using the in vivo protein production and delivery system described the present invention. GLP-1 derivatives include truncated derivatives GLP-1(7-37), GLP-1(7-36), GLP-1(7-35), GLP-1(7-truncated carboxyl-terminal amidated derivatives and derivatives of GLP-1 which have amino acid substitutions, deletions, additions, or other alterations (e.g., addition of a non-amino acid component) which result in biological activity or stability in the blood which is substantially the same as that of a truncated GLP-1 derivative or enhanced biological activity or stability in the blood (greater than that of a truncated GLP-1 derivative). As used herein, the term GLP-1 derivative includes all of the above-described molecules. The term GLP-1 related peptide, as used herein, includes GLP-1 and GLP-1 derivatives. GLP-1 derivatives, also known as insulinotropins or incretins, are normally secreted into the circulation by cells in the gastrointestinal tract. In vivo studies have demonstrated that these peptides function to stimulate insulin secretion and inhibit glucagon secretion from the endocrine pancreas, as well as increase insulin sensitivity in peripheral tissues [Goke, R. et al. (1991) Eur. J. Clin. Inv. 21:135-144; Gutniak, M. et al. (1992) New Engl. J. Med. 326:1316-1322]. Patients with non-insulin dependent diabetes mellitus (NIDDM) are often treated with high levels of insulin to compensate for their decreased insulin sensitivity. Thus, the stimulation of insulin release and the increase in insulin sensitivity by GLP-1 derivatives would be beneficial for NIDDM patients. Of particular importance is the fact that the insulinotropin-induced stimulation of insulin secretion is strongly dependent on glucose levels, suggesting that these peptides act in response to increases in blood glucose in vivo to potentiate insulin release and, ultimately, lower blood glucose.

The present invention will now be illustrated by the following examples, which are not intended to be limiting in any way.

EXAMPLES

Example 1

Isolation of Fibroblasts a. Source of Fibroblasts

Human fibroblasts can be obtained from a variety of tissues, including biopsy specimens derived from liver, kidney, lung and skin. The procedures presented here are optimized for the isolation of skin fibroblasts, which are readily obtained from individuals of any age with minimal discomfort and risk (embryonic and fetal fibroblasts may be isolated using this protocol as well). Minor modifications to the protocol can be made if the isolation of fibroblasts from other tissues is desired.

Human skin is obtained following circumcision or punch biopsy. The specimen consists of three major components: the epidermal and dermal layers of the skin itself, and a fascial layer that adheres to the dermal layer. Fibroblasts can be isolated from either the dermal or fascial layers.

b. Isolation of Human Fascial Fibroblasts

Approximately 3 $cm^2$ tissue is placed into approximately 10 ml of wash solution (Hank's Balanced Salt Solution containing 100 units/ml penicillin G, 100 µg/ml streptomycin sulfate, and 0.5 µg/ml Fungisone) and subjected to gentle agitation for a total of three 10-minute washes at room temperature. The tissue is then transferred to a 100 mm tissue culture dish containing 10 ml digestion solution (wash solution containing 0.1 units/ml collagenase A, 2.4 units/ml grade II Dispase).

Under a dissecting microscope, the skin is adjusted such that the epidermis is facing down. The fascial tissue is separated from the dermal and epidermal tissue by blunt dissection. The fascial tissue is then cut into small fragments (less than 1 $mm^2$) and incubated on a rotating platform for 30 minutes at 37° C. The enzyme/cell suspension is removed and saved, an additional 10 cc of digestion solution is added to the remaining fragments of tissue, and the tissue is reincubated for 30 minutes at 37° C. The enzyme/cell suspensions are pooled, passed through a 15-gauge needle several times, and passed through a Cellector Sieve (Sigma) fitted with a 150-mesh screen. The cell suspension is centrifuged at 1100 rpm for 15 minutes at room temperature. The supernatant is aspirated and the disaggregated cells resuspended in 10 ml of nutrient medium (see below). Fibroblast cultures are initiated on tissue culture treated flasks (Corning) at a density of approximately 40,000 cells/$cm^2$.

c. Isolation of Human Dermal Fibroblasts

Fascia is removed from skin biopsy or circumcision specimen as described above and the skin is cut into small fragments less than 0.5 $cm^2$. The tissue is incubated with 0.25% trypsin for 60 minutes at 37° C. (alternatively, the tissue can be incubated in trypsin for 18 hours at 4° C.). Under the dissecting microscope, the dermis and epidermis are separated. Dermal fibroblasts are then isolated as described above for fascial fibroblasts.

d. Isolation of Rabbit Fibroblasts

The procedure is essentially as described above. Skin should be removed from areas that have been shaved and washed with a germicidial solution and surgically prepared using accepted procedures.

Example 2

Culturing of Fibroblasts a. Culturing of Human Fibroblasts

When confluent, the primary culture is trypsinized using standard methods and seeded at approximately 10,000 cells/$cm^2$. The cells are cultured at 37° C. in humidified air containing 5% $CO_2$. Human fibroblast nutrient medium (containing DMEM, high glucose with sodium pyruvate, 10-15% calf serum, 20 mM HEPES, 20 mM L-glutamine, 50 units/ml penicillin G, and 10 µg/ml streptomycin sulfate) is changed twice weekly.

b. Culturing of Rabbit Fibroblasts

The cells are trypsinized and cultured as described for human fibroblasts. Rabbit fibroblast nutrient medium consists of a 1:1 solution of MCDB-110 (Sigma) with 20% calf serum and conditioned medium. Conditioned medium is essentially human fibroblast nutrient medium (with 15% calf serum) removed from rabbit fibroblasts grown in mass culture for 2-3 days.

Example 3

Construction of a Plasmid (pXEPO1) Containing the Human Erythropoietin Gene Under the Control of the Mouse Metallothionein Promoter The expression plasmid pXEPO1 has the hEPO gene under the transcriptional control of the mouse metallothionein (mMT) promoter. pXEPO1 is constructed as follows: Plasmid pUC19 (ATCC #37254) is digested with KpnI and BamHI and ligated to a 0.7 kb KpnI-BglII fragment containing the mouse metallothionein promoter [Hamer, D. H. and Walling, M., J. Mol. Appl. Gen., 1:273-288 (1982). This fragment can also be isolated by known methods from mouse genomic DNA using PCR primers designed from analysis of mMT sequences available from Genbank; i.e. MUSMTI, MUSMTIP, MUSMTIPRM]. The resulting clone is designated pXQM2.

The hEPO gene was isolated by from a bacteriophage lambda clone containing the entire hEPO gene. This bacteriophage was isolated by screening a human Sau3Apartial genomic DNA library (Stratagene) constructed in the lambda vector LAMBDA DASH with 0.77 kb fragment of the human gene. This 0.77 kb fragment was amplified from human genomic DNA using the primers shown below in the polymerase chain reaction (PCR).

```
HUMAN EPO PCR PRIMERS:

Oligo hEPO-1: 5'GTTTGCTCAGCTTGGTGCTTG  (SEQ ID NO:1)
(positions 2214-2234 in the Genbank HUMERPA
sequence)

Oligo hEPO-2: 5'TCAAGTTGGCCCTGTGACAT   (SEQ ID NO:2)
(positions 2986-2967 in the Genbank HUMERPA
sequence)
```

The amplified fragment, encompassing exons 4 and 5 of the human EPO gene, was radiolabelled and used to screen the human genomic DNA library. Phage with a 5.4 kb HindIII-BamHI fragment containing the entire human EPO gene were assumed to contain the entire gene, based on published DNA sequence and restriction enzyme mapping data [Lin, F-K., et al., Proc. Natl. Acad. Sci. USA, 82:7580-7584 (1985)].

A 4.8 kb BstEII-BamHI fragment (BstEII site is at position 580 in Genbank HUMERPA sequence; the BamHI site is 4.8 kb 3' of this site, outside of the sequenced region) was isolated from the bacteriophage clone. The purified fragment is made blunt-ended by treatment with the Klenow fragment of *E. coli* DNA polymerase and ligated to HincII digested pXQM2, which cuts in the pUC19-derived polylinker adjacent to the 3' side of the subcloned mMT promoter. One orientation, in which the ablated BstEII site is proximal to the mMT promoter, was identified by restriction mapping and designated pXEPO1 (FIG. 1).

Example 4

Transfection of Primary and Secondary Fibroblasts with Exogenous DNA and a Selectable Marker Gene by Electroporation and Microinjection To prepare cells for electroporation, exponentially growing or early stationary phase fibroblasts are trypsinized and rinsed from the plastic surface with nutrient medium. An aliquot of the cell suspension is removed for counting, and the remaining cells are subjected to centrifugation as described above. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Supercoiled plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 msec should be observed.

Electroporated cells are maintained at room temperature for approximately 5 minutes, and the contents of the cuvette are then gently removed with a sterile transfer pipette. The cells are added directly to 10 ml of prewarmed nutrient media (as above with 15% calf serum) in a 10 cm dish and incubated as described above. The following day, the media is aspirated and replaced with 10 ml of fresh media and incubated for a further 16-24 hours. Subculture of cells to determine cloning efficiency and to select for G418-resistant colonies is performed the following day. Cells are trypsinized, counted and plated; typically, fibroblasts are plated at $10^3$ cells/10 cm dish for the determination of cloning efficiency and at $1-2 \times 10^4$ cells/10 cm dish for G418 selection.

Human fibroblasts are selected for G418 resistance in medium consisting of 300-400 µg/ml G418 (Geneticin, disulfate salt with a potency of approximately 50%; Gibco) in fibroblasts nutrient media (with 15% calf serum). Cloning efficiency is determined in the absence of G418. The plated cells are incubated for 12-14 days, at which time colonies are fixed with formalin, stained with crystal violet and counted (for cloning efficiency plates) or isolated using cloning cylinders (for G418 plates). Electroporation and selection of rabbit fibroblasts is performed essentially as described for human fibroblasts, with the exception of the nutrient media used. Rabbit fibroblasts are selected for G418 resistance in medium containing 1 mg/ml G418.

Fibroblasts were isolated from freshly excised human foreskins. Cultures were seeded at 50,000 cells/cm² in DMEM+ 10% calf serum. When cultures became confluent fibroblasts were harvested by trypsinization and transfected by electroporation. Electroporation conditions were evaluated by transfection with the plasmid pcDNEO. A representative electroporation experiment using near optimal conditions (60 µg of plasmid pcDNEO at an electroporation voltage of 250 volts and a capacitance setting of 960 µFarads) resulted in one $G418^r$ colony per 588 treated cells (0.17% of all cells treated), or one $G418^r$ colony per 71 clonable cells (1.4%).

When nine separate electroporation experiments at near optimal conditions (60 µg of plasmid pcDNEO at an electroporation voltage of 300 volts and a capacitance setting of 960 µFarads) were performed, an average of one $G418^r$ colony per 1,899 treated cells (0.05%) was observed, with a range of 1/882 to 1/7,500 treated cells. This corresponds to an average of one $G418^R$ colony per 38 clonable cells (2.6%).

Low passage primary human fibroblasts were converted to hGH expressing cells by co-transfection with plasmids pcDNEO and pXGH5 [Selden, R. F. et al., Mol. Cell. Biol., 6:3173-3179 (1986)]. Typically, 60 µg of an equimolar mixture of the two plasmids were transfected at near optimal conditions (electroporation voltage of 300 volts and a capacitance setting of 960 µFarads). The results of such an experiment resulted in one $G418^r$ colony per 14,705 treated cells.

hGH expression data for these and other cells isolated under identical transfection conditions are summarized below. Ultimately, 98% of all $G418^r$ colonies could be expanded to generate mass cultures.

| | |
|---|---|
| Number of $G418^r$ Clones Analyzed | 154 |
| Number of $G418^r$/hGH Expressing Clones | 65 |
| Average hGH Expression Level | 2.3 µg hGH/$10^6$ Cells/24 hours |
| Maximum hGH Expression Level | 23.0 µg hGH/$10^6$ Cells/24 hours |

Stable transfectants also have been generated by electroporation of primary or secondary human fibroblasts with pXGH301, a DNA construct in which the neo and hGH genes are present on the same plasmid molecule (Example 3). For example, $1.5 \times 10^6$ cells were electroporated with 60 µg pXGH301 at 300 volts and 960 µFarads. G418 resistant colonies were isolated from transfected secondary fibroblasts at a frequency of 652 G418 resistant colonies per $1.5 \times 10^6$ treated cells (1 per 2299 treated cells). Approximately 59% of these colonies express hGH.

Figure 3:
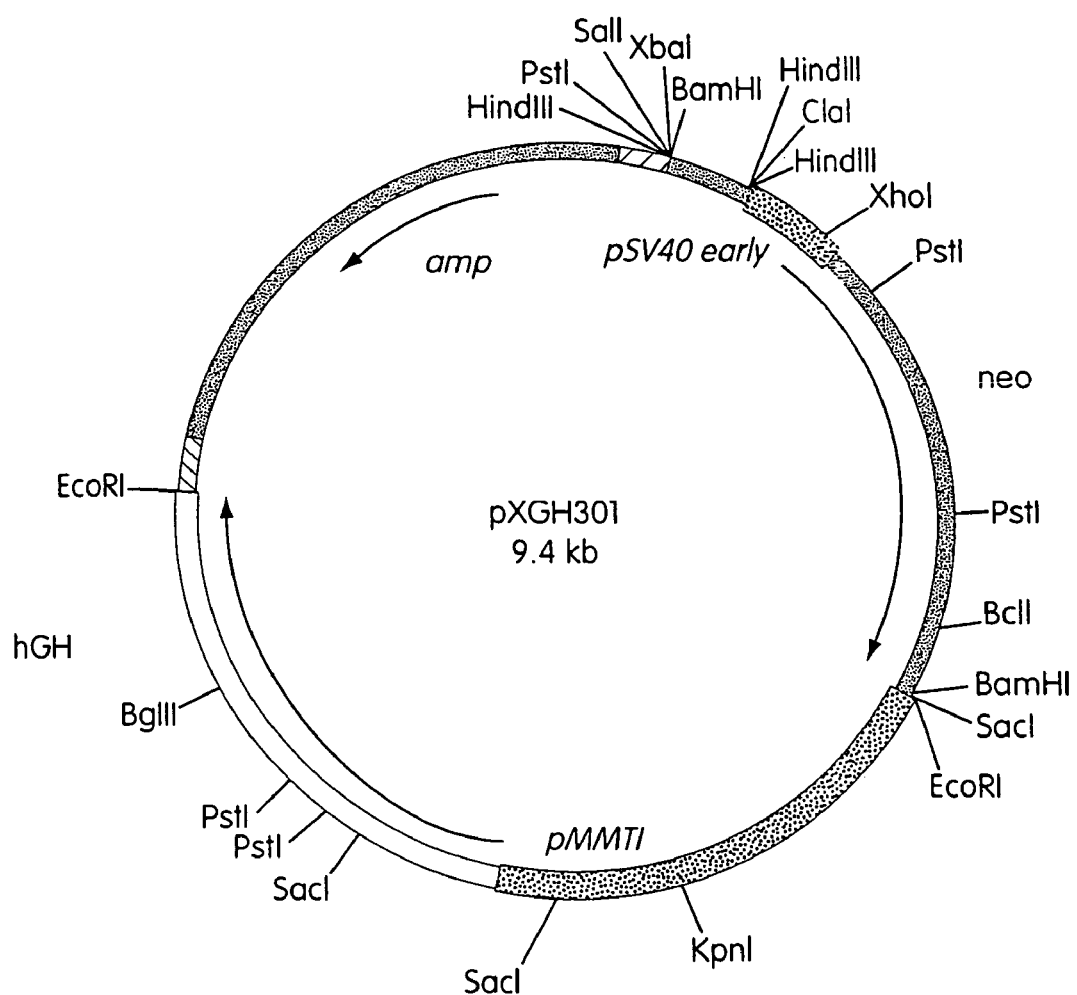
FIG. 3 is a schematic representation of plasmid pXGH301. This plasmid contains both the human growth hormone (hGH) and neo resistance genes. Arrows indicate the directions of transcription of the various genes. The positions of restriction endonuclease recognition sites, the mouse metallothionein promoter (PMMT1), the amp resistance gene, and the SV40 early promoter (pSV40 early) are indicated.

Primary and secondary human fibroblasts can also be transfected by direct injection of DNA into cell nuclei. The ability of primary and secondary human foreskin fibroblasts to be stably transfected by this method has not been previously reported. The 8 kb HindIII fragment from plasmid RV6.9h (Zheng, H. et al., Proc. Natl. Acad. Sci. USA 88:18 8067-8071 (1991)) was purified by gel electrophoresis and passage through an anion exchange column (QIAGEN Inc.). DNA at (10 µg/ml) was injected into primary or secondary human foreskin fibroblasts using 0.1 µm outer diameter glass needles. 41 $G418^r$ clones were isolated after injection of 2,000 cells (1 in 49 starting cells).

hGH expressing clones were also generated by microinjection. Plasmid pXGH301 (FIG. 3) was linearized by ScaI digestion (which cuts once within the $amp^r$ gene in the pUC12 backbone), purified by passage through an anion exchange column (QIAGEN Inc.), and injected into secondary human foreskin fibroblasts using 0.1 µm outer diameter glass needles. Several DNA concentrations were used, ranging from 2.5-20 µg pXGH301/ml. Twenty G418 resistant clones were isolated after microinjection into 2,100 cells (1 in $10^5$ starting cells). The fraction of G418$^r$ cells, is approximately 1% of all cells treated. Nine of 10 clones analyzed were expressing hGH, with average hGH expression being 0.6 µg/$10^6$ cells/24 hours for clones isolated in this experiment, and 3 clones were expanded for studying long-term expression of hGH. All 3 were expressing hGH stably, with hGH still being produced through 33, 44, and 73 mpd for the 3 strains, respectively.

Example 5

In Vitro hEPO Production by Transfected Secondary Human and Rabbit Skin Fibroblasts 1. Human Skin Fibroblasts Fibroblasts were isolated from freshly excised human skin fibroblasts and cultured in DMEM+15% calf serum. Electroporation (250 volts, 960 µFarads) with 60 µg of an equimolar mixture of pcDNEO and pXEPO1 was performed on passage 1 cells and treated cells were selected in G418-containing medium (300 µg/ml G418). Colonies were isolated and expanded using standard methods. Data derived from an analysis of fifty-six individual clones is shown in Table 1 below. Cells were maintained in G418 (300 µg/ml G418) in DMEM+15% calf serum and subcultured at a seeding density of 10,000 cells/cm$^2$. Culture medium was changed 24 hours prior to harvesting the cells for passaging. At the time of passage, an aliquot of the culture medium was removed for hEPO assay and the cells were then harvested, counted, and reseeded. hEPO concentration in the medium was determined using a commercially available ELISA (R & D Systems). hEPO levels are expressed as mU/$10^6$ cells/24 hours, and expression levels ranged from 69 to 55,591 mU/$10^6$ cells/24 hours 19% of all G418-resistant colonies expressed detectable levels of hEPO.

TABLE 1 hEPO EXPRESSION IN FIFTY-SIX INDEPENDENT SECONDARY HUMAN FIBROBLAST CLONES ISOLATED BY CO-TRANSFECTION WITH pcDNEO AND pXEPO1

| HEPO Expression Level (mU/$10^6$ cells/24 hours) | Number of Clones |
|---|---|
| <1,000 | 10 |
| 1,000-10,000 | 28 |
| 10,000-50,000 | 17 |
| >50,000 | 1 |

Clonally derived human fibroblasts isolated by co-transfection with pcDneo and pXEPO1 were analyzed for the glycosylation state of secreted hEPO. Media was collected from hEPO producing cells and immunoprecipitated with a mouse monoclonal antibody (Genzyme Corporation) specific for human erythropoietin. The immunoprecipitated material was subject to electrophoresis on a 12.5% polyacrylamide gel and transferred to a PVDF membrane (Millipore). The membrane was probed with the same anti-hEPO monoclonal antibody used for immunoprecipitation and was subsequently treated with an HRP-conjugated sheep anti-mouse IgG antisera (Cappel), followed by luminescent detection (ECL Western blotting detection kit; Amersham) to visualize hEPO through the production of a fluorescent product.

Figure 5A:
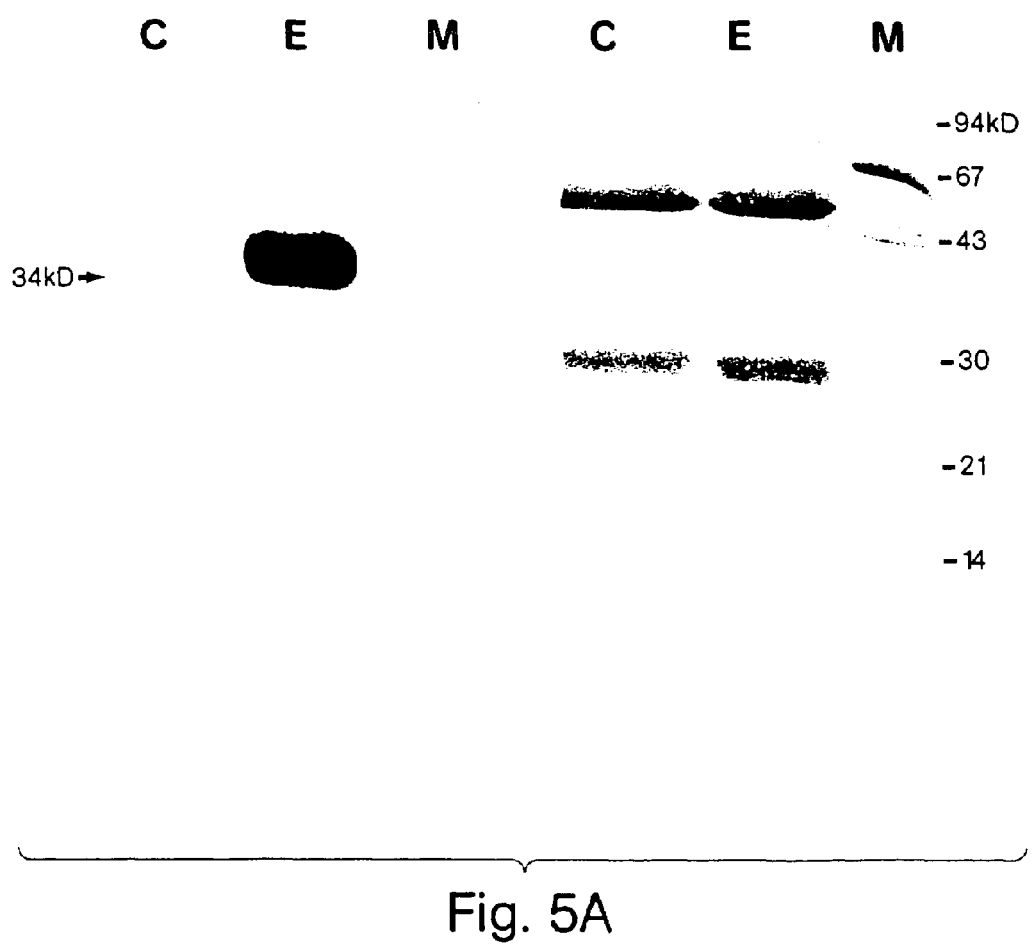
FIG. 5A shows results of Western blot analysis of hEPO secreted by normal human fibroblasts cotransfected with pXEPO1 and pcDNEO. The left panel shows the Western analysis and the right panel shows a photograph of the Coomassie blue stained gel. Lanes C, E, and M signify Control sample (supernatant from untransfected human fibroblasts), Experimental sample (supernatant from a clonal strain of human fibroblasts expressing hEPO), and marker lanes, respectively.
Figure 5B:
FIG. 5B shows results of Western blot analysis of hEPO secreted by normal human fibroblasts cotransfected with pXEPO1 and pcDNEO. Supernatant from a clonal strain of human fibroblasts expressing hEPO (lane 1) was further analyzed for glycosylation by treatment with endoglycosidase-F (lane 2), neuraminidase (lane 3), and O-glycanase (lane 4).
Figure 5B:
Figure 5B:
Figure 5B:

As shown in FIG. 5A, a molecule with a molecular mass of approximately 34 kd reacts with an antibody specific for human erythropoietin. This is the expected size for naturally occurring, fully glycosylated human erythropoietin.

hEPO produced by transfected human fibroblast clones was further analyzed to determine if the secreted material had both N- and O-linked glycosylation characteristic of natural human erythropoietin isolated from urine or recombinant hEPO produced by chinese hamster ovary cells. FIG. 5B shows a Western blot of the untreated cell supernatant (lane 1), the supernatant treated with endoglycosidase-F [(New England Nuclear); lane 2], the supernatant treated with neuraminidase [Genzyme); (lane 3)], and the supernatant treated with O-glycanase [(Genzyme); (lane 4)]. Treatment with endoglycosidase-F results in a shift in molecular weight from 34 kd to approximately 27 kd. Treatment with neuraminidase results in a barely detectable shift in band position, while treatment with O-glycanase further shifts the size of the immunoreactive band down to approximately 18.5 kd. These results are indistinguishable from those obtained with natural human erythropoietin isolated from urine or recombinant hEPO produced by Chinese hamster ovary cells (Browne, J. K. et al., Cold Spring Harbor Symp. Quant. Biol. 51:693-702 (1986)).

2. Rabbit Fibroblasts

Fibroblasts were isolated from freshly excised rabbit skin and cultured in DMEM 10% calf serum. Electroporation (250 volts, 960 µFarads) with 60 µg of an equimolar mixture of pcDNEO and pXEPO1 was performed and treated cells were selected in G418-containing rabbit fibroblast growth medium (1 mg/ml G418; Example 2). Colonies were isolated and expanded using standard methods, and the resulting secondary cell strains were analyzed for hEPO expression. Data derived from forty-nine independent rabbit fibroblast clones is shown in Table 2, below. Expression levels in these clones ranged from 43 to 2,900,000 mU/$10^6$ cells/24 hours, and 72% of all G418-resistant clones expressed detectable levels of hEPO.

TABLE 2 hEPO EXPRESSION IN FORTY-NINE INDEPENDENT SECONDARY RABBIT FIBROBLAST CLONES ISOLATED BY CO-TRANSFECTION WITH pcDNEO AND pEEPO

| HEPO Expression Level (mU/$10^6$ cells/24 hours) | Number of Clones |
|---|---|
| <1,000 | 1 |
| 1,000-10,000 | 3 |
| 10,000-50,000 | 7 |
| 50,000-500,000 | 19 |
| >500,000 | 19 |

Example 6

Construction of a Plasmid Containing Both the Human EPO Gene and the Neomycin Resistance Gene A 6.9 kb HindIII fragment extending from positions 11,960-18,869 in the HPRT sequence [Genbank entry HUM-HPRTB; Edwards, A. et al., Genomics, 6:593-608 (1990)] and including exons 2 and 3 of the HPRT gene, is subcloned into the HindIII site of pUC12. The resulting clone is cleaved at the unique XhoI site in exon 3 of the HPRT gene fragment and the 1.1 kb SalI-XhoI fragment containing the neo gene from pMC1NEO (Stratagene) is inserted, disrupting the coding sequence of exon 3. One orientation, with the direction of neo transcription opposite that of HPRT transcription was chosen and designated pE3Neo. pE3neo has a unique XhoI site at the junction of HPRT sequences and the 5' side of the neogene. pE3neo is cut with XhoI and made blunt-ended by treatment with the Klenow fragment of E. coli DNA polymerase.

To insert the hEPO gene into the neo selection plasmid pE3Neo, a 5.1 kb EcoRI-HindIII fragment was isolated from plasmid pXEPO1 (Example 3; FIG. 1). The EcoRI site is located adjacent to the 5' side of the mMT promoter, and the HindIII site is located 5.1 kb away, 3' to the hEPO coding region. The purified Fragment is made blunt-ended by treatment with Klenow fragment of E. coli DNA polymerase and ligated to the XhoI digested and blunt-ended pE3neo fragment described above. After transformation into E. coli, a plasmid with one copy of the mMT-hEPO fragment inserted into pE3neo was identified by restriction enzyme analysis in which the hEPO gene is transcribed in the same orientation as the adjacent neogene. This plasmid was designated pE3neoEPO. In addition to allowing direct selection of hEPO expressing G418$^r$ clones, this fragment may also be used in gene targeting to direct the integration of the hEPO gene to the human HPRT locus.

Example 7

Isolation of Human Fibroblast Clones Expressing Hepo Gene and a Selectable Marker (pE3neoEPO)

Fibroblasts were isolated from freshly excised human skin fibroblasts and cultured in DMEM+15% calf serum. Electroporation (250 volts, 960 µFarads) with 60 µg of supercoiled pE3neoEPO was performed on passage 1 cells and treated cells were selected in G418-containing medium (300 µg/ml G418). Colonies were isolated and expanded using standard methods. Data derived from an analysis of twenty-six individual clones is shown in Table 3, below. Cells were maintained in G418 (300 µg/ml G418) in DMEM+15% calf serum and subcultured at a seeding density of 10,000 cells/cm$^2$. Culture medium was changed 24 hours prior to harvesting the cells for passaging. At the time of passage an aliquot of the culture medium was removed for hEPO assay and the cells were then harvested, counted, and reseeded. hEPO concentration in the medium was determined using a commercially available ELISA (R and D Systems). hEPO levels are expressed as mU hEPO/10$^6$ cells/24 hours, and expression levels ranged from 240 to 961,620 mU/10$^6$ cells/24 hours 89% of all G418-resistant clones expressed detectable levels of hEPO.

TABLE 3 hEPO EXPRESSION IN TWENTY-SIX INDEPENDENT SECONDARY HUMAN FIBROBLAST CLONES ISOLATED BY CO-TRANSFECTION WITH pE3neo-EPO

| HEPO Expression Level (mU/10$^6$ cells/24 hours) | Number of Clones |
|---|---|
| <1,000 | 2 |
| 1,000-10,000 | 2 |
| 10,000-50,000 | 9 |
| 50,000-500,000 | 12 |
| >500,000 | 1 | hEPO expressing human fibroblast clones are also isolated by electroporation with 60 µg of HindIII digested pE3neoEPO. hEPO expressing rabbit fibroblast clones are isolated using plasmid pE3neoEPO under identical transfection conditions, with the exception that rabbit fibroblast clones are selected in rabbit fibroblast growth medium (Example 2) containing 1 mg/ml G418.

Example 8

Isolation of Transfectants in the Absence of Selection

The high frequency of transfection in human fibroblasts (greater than 1% stable transfectant per clonable cell; Example 4) indicates that it should be possible to isolate cell clones that have stably incorporated exogenous DNA without the use of a selective agent. Stable transfection of primary fibroblasts with the plasmid pXEPO1 should render recipient fibroblasts capable of secreting human erythropoietin into the surrounding medium. Therefore, an ELISA for hEPO (or for any expressed protein of therapeutic interest) can be used as a simple and rapid screen for transfectants. Alternatively, it should be possible to determine the true frequency of stable integration of exogenous DNA using a screening method such as PCR which does not necessarily rely on expression of transfected DNA.

1. Primary Human Fibroblasts

Approximately 2.0×10$^6$ human cells that were freshly dissociated from tissue are electroporated with 60 µg of pXEPO1 at 300 volts, 960 µFarads. Cells are plated immediately in a 100 mm tissue culture dish containing 10 ml of prewarmed medium and incubated at 37° C. in a humidified 5% CO$_2$ atmosphere. Two days following transfection, 5×10$^3$ cells are subcultured into a 24 well cloning plate (Bellco Glass Co.). Each well of the 24 well plate contained 16 smaller wells (384 wells/plate). Eight days after plating into the 24 large wells, media is screened for hEPO expression via ELISA. A second, confirming assay, is done in which media from wells exhibiting hEPO expression is aspirated out, replaced with fresh media and assayed for hEPO 24 hours later. Colony counts at this stage should reveal approximately 10 colonies per large well.

Individual colonies in each of the 16 small wells within one of the hEPO-positive larger wells are trypsinized and transferred to wells of a 96 well plate. Three days later each of those wells are assayed for hEPO expression. Cells from hEPO positive cells are expanded for further study. This experiment may also be performed using secondary human foreskin fibroblasts.

2. Primary Rabbit Fibroblasts

Passage 1 rabbit skin cells were transfected with pXEPO1. The electroporation conditions were identical to the human tissue electroporation described above. 1×10$^3$ cells are subcultured into a 384 well plate. Seven days later hGH assays are performed on media from each of the 24 large wells. Cells in each of the small wells in hEPO-positive large wells are trypsinized and transferred to wells of a 96 well plate. Three days later each of these wells are assayed for hEPO expression. Cells from hEPO positive cells are expanded for further study. This experiment may also be performed using secondary rabbit skin fibroblasts.

Example 9

Stable Transfection of Primary Human Fibroblasts by Microinjection

Direct injection of DNA into cell nuclei is another method for stably transfecting cells. The ability of primary and secondary human foreskin fibroblasts to be stably transfected by this method is described in Example 4, but has not been previously reported in the literature. The 13.1 kb HindIII fragment from plasmid pE3neoEPO is purified by gel electrophoresis and passed through an anion exchange column (QIAGEN Inc.). This fragment contains the human EPO and bacterial neo genes, flanked on both sides with human HPRT sequences. DNA at (10 µg/ml) is injected into primary or secondary human foreskin fibroblasts using 0.1 µm diameter glass needles. G418$^r$ clones are isolated approximately 12-14 days after injection. Alternatively, the total HindIII digest of pE3neoEPO, as well as linearized or supercoiled pE3neoEPO may be injected to isolate hEPO expressing cells.

Example 10

Expression of Biologically Active Human Erythropoietin in Mice

The mouse provides a valuable system to study implants of genetically engineered cells for their ability to deliver therapeutically useful proteins to an animal's general circulation. The relative immunoincompetence of nude mice allow xenogeneic implants to retain biologic function and may allow certain primary and secondary rabbit fibroblasts to survive in vivo for extended periods.

For implantation of cells into the subrenal capsule, mice are given intraperitoneal injection of Avertin at a dose of 0.0175 ml/g body weight. The kidney (generally the left kidney) is approached through an 8-10 mm incision made approximately 3 mm below the rib cage. The skin, abdominal musculature, peritoneum, and peri-renal fascia are retracted to expose the kidney. A small forcept is used to pull the kidney out of the abdominal cavity. A 27-gauge hypodermic needle is used to make a small opening in the renal capsule. Using a 20-gauge I.V. catheter, cells to be implanted (typically 3 million cells in a volume of 5-10 µl) are withdrawn into a 1 ml syringe and slowly ejected under the renal capsule. Care is taken to ensure that the cells are released distal to the opening in the renal capsule. The incision is closed with one staple through the musculature and the skin. Blood is collected after placing the mouse in a large beaker containing methoxyflurane until light anesthesia is achieved. The tip of a Pasteur pipette is placed between the eye and the periorbital space to collect blood from the orbital sinus. Serum hEPO levels are determined using a commercially available kit (R and D Systems). An aliquot of blood is also drawn into EDTA coated capillary tubes (Statspin, Norwood, Mass.) for determination of hematocrit levels.

Figure 6A:
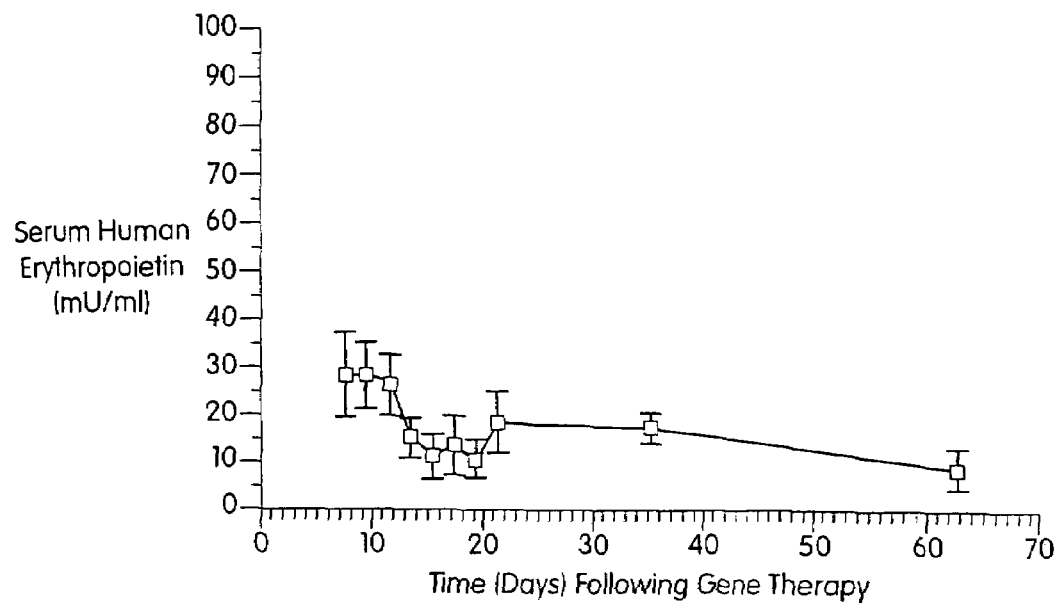
FIG. 6A shows results of an assay to detect hEPO in the serum of mice implanted with transfected rabbit fibroblasts expressing hEPO.
Figure 6B:
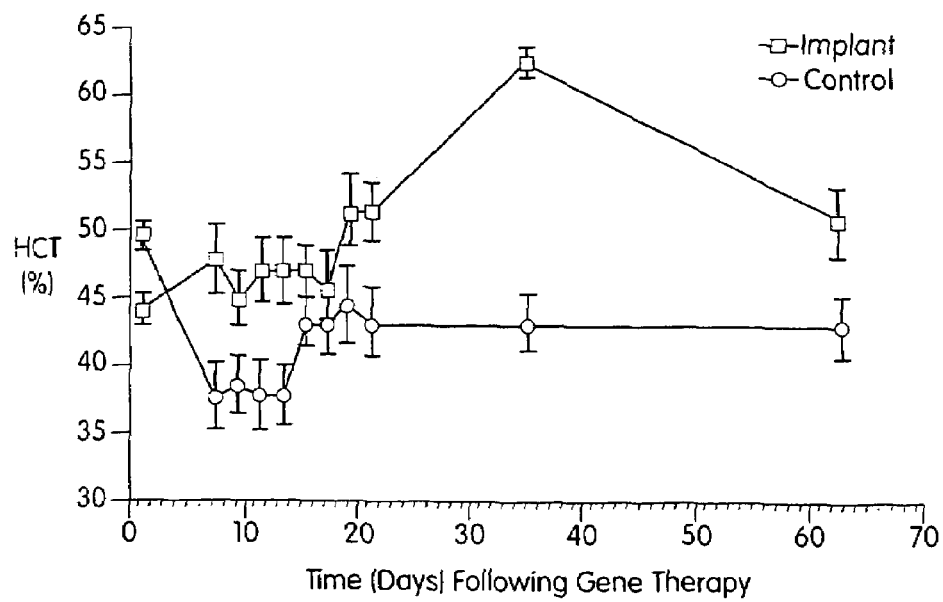
FIG. 6B shows hematocrit (HCT) levels in control mice and mice implanted with transfected rabbit fibroblasts expressing hEPO.

A clonal strain of rabbit skin fibroblasts was isolated by the methods described in Example 5. One clone, designated RF115-D4, was determined to be stably transfected with the human EPO gene and expressed approximately 786,000 mU hEPO/10$^6$ cells/24 hours. Three million cells were implanted into the subrenal capsule in each of six nude mice. Approximately 400 µl of blood was drawn on days 1 and 7 after implantation and on every other day thereafter until day 21. During this time an equal volume of saline solution was injected after bleeding to prevent hypotonic shock. Blood was drawn weekly there after until day 63. An identical bleeding schedule was used on ten mice that had no cells implanted. FIG. 6A shows the effect of these treatments on blood hematocrit (HCT), a commonly used indicator of red blood cell number, in implanted and control animals. In control animals, HCT drops dramatically by day 7, followed by a return to approximately normal levels by day 15. In contrast, animals receiving implants of the hEPO expressing cells showed elevated HCT levels by day 7. HCT remained elevated through day 63, reaching a peak of 64%, or 1.4 times higher than the day 1 level of 45%, on day 35 after implantation. As shown in FIG. 6B, immunoreactive hEPO was readily detectable in the blood of implanted animals (the sensitivity of the hEPO ELISA has been determined to be 2 mU/ml by the kit's manufacturer (R and D Systems) and endogenous mouse EPO shows no cross-reactivity with the antibodies used in the ELISA kit). hEPO levels in the implanted animals dropped gradually, from 29 to 9 mU/ml, from days 7 to 63 postimplantation.

This Example clearly demonstrates that normal skin fibroblasts that have been genetically engineered to express and secrete hEPO can: 1) survive in vivo to deliver hEPO to an animals systemic circulation for up to 2 months, and 2) the hEPO produced is biologically functional, serving to prevent the drop in hematocrit observed in the frequently bled control animals, and resulting in a net increase in HCT even when animals were challenged with a bleeding schedule that produces an anemic response in control animals.

Example 11

Expression of GLP-1(7-37) from Secondary Human Skin Fibroblasts Strains after Transfection with a GLP-1(7-37) Expression Plasmid The portion of GLP-1 from amino acid residues 7 to 37 [GLP-1(7-37); encoded by base pairs 7214 to 7306 in Genbank sequence HUMGLUCG2] has been demonstrated to have insulinotropin activity in vivo. Plasmid pXGLP1 is constructed such that the GLP-1(7-37) moiety is fused at its N-terminus to a 26 amino acid signal peptide derived from human growth hormone for efficient transport through the endoplasmic reticulum. The fusion protein is cleaved immediately C-terminal to residue 26 prior to secretion, such that the secreted product consists solely of residues 7-37 of GLP-1. Expression of the signal peptide: GLP-1(1-37) fusion protein is controlled by the mouse metallothionein promoter.

Plasmid pXGLP1 is constructed as follows: Plasmid PXGH5 [Selden, R. F. et al., Mol. Cell. Biol. 6:3173-3179 (1986)] is digested with SmaI and ligated to a double-stranded oligonucleotide containing a BglII site (BglII linkers; New England Biolabs). The ligated product is digested with BglII and EcoRI and the 0.32 kb fragment corresponding to the 3'-untranslated region of the human growth hormone gene is isolated (with a BglII linker attached to the SmaI site lying at position 6698 in Genbank entry HUMGHCSA). The hGH fragment can also be isolated by known methods from human genomic DNA using PCR primers designed to amplify the sequence between positions 6698 to 7321 in Genbank entry HUMGHCSA. A 1.45 EcoRI-BglII fragment containing the mouse metallothionein (mMT) promoter [Hamer, D. H. and Walling, M., J. Mol. Appl. Gen., 1:273-288 (1982)] is next isolated. The mouse metallothionein promoter may be isolated by known methods from mouse genomic DNA using PCR primers designed from analysis of mMT sequences available from Genbank (i.e. Genbank entries MUSMTI, MUSMTIP, and MUSMTIPRM). Plasmid pUCIg (ATCC #37254) is digested with EcoRI and treated with bacterial alkaline phosphatase. The treated plasmid is ligated with the hGH and mMT fragments described above. The resulting plasmid has a single copy of each the mouse metallothionein promoter and the 3' untranslated region of hGH joined at a BglII site. This plasmid, designated pX1 is digested with BglII and the full-length linear product is purified by gel electrophoresis.

Oligonucleotides 11.1 and 11.2 are used to amplify a DNA sequence encoding amino acids 7-37 of GLP-1 from human genomic DNA by PCR. The amplified product (104 bp) is purified and mixed with pXGH5 and oligonucleotides 11.2, 11.3, 11.4, and 11.5 and subject to PCR. Oligonucleotides 11.3 and 11.4 are complementary and correspond to the desired junction between the hGH signal peptide and GLP-1 amino acid residue 7. The 500 base pair amplification product contains 5'-untranslated, exon 1, intron 1, and part of exon 2 sequences from hGH (nucleotides 5168 to 5562 in Genbank entry HUMGHCSA) fused to a sequence encoding GLP-1 residues 7-37 followed by a stop codon. The fragment, by design, is flanked on both ends by BamHI sites. The fragment is cleaved with BamHI and ligated to the BglII digest of pX1 described above. Ligation products are analyzed to identify those with one copy of the hGH-GLP-1(7-37) fusion product inserted at the BglII site separating the mMT promoter and the 3'-untranslated hGH sequence in pX1, such that GLP-1 residue 37 is distal to the mMT promoter.

followed, such that the final product is lacking the C-terminal glycine residue characteristic of GLP-1(7-37). Alternatively, this terminal glycine residue may be removed in vivo by the activity of a peptidyl-glycine alpha-amidating enzyme to produce the insulinotropin GLP-1(7-36) amide.

Plasmid pXGLP1 is co-transfected into primary human skin fibroblasts with plasmid pcDNEO exactly as described for pXEPO1 and pcDNEO in Example 5. Clones are selected in G418-containing medium, transferred to 96-well plates, and assayed for GLP-1(7-37) activity or immunoreactivity in cell supernatants. GLP-1(7-37) activity is determined by incubation of cell supernatants with rat insulinoma RINm5F cells and measuring the ability of the supernatants to induce insulin secretion from these cells using a commercially available insulin radioimmunoassay (Coat-a-Count Insulin, DPC, Los Angeles, Calif.). GLP-1(7-37) antigen is determined using a commercially available antisera against GLP-1 (Peninsula Laboratories, Belmont, Calif.). GLP-1(7-37) positive clones are expanded for implantation into nude mice as

| OLIGONUCLEOTIDES FOR AMPLIFICATION OF hGH-GLP-1(7-37) FUSION GENE | |
|---|---|
| 11.1 5'CATGCTGAAG GGACCTTTAC CAGT | (SEQ ID NO:3) |
| 11.2 5'TT<u>GGATCC</u>TT ATCCTCGGCC TTTCACCAGC CA<br>     BamHI | (SEQ ID NO:4) |
| 11.3 5'GGCTTCAAGA GGGCAGTGCC CATGCTGAAG GGACCTTTAC CAGT | (SEQ ID NO:5) |
| 11.4 5'ACTGGTAAAG GTCCCTTCAG CATGGGCACT GCCCTCTTGA AGCC | (SEQ ID NO:6) |
| 11.5 5'AA<u>GGATCC</u>CA AGGCCCAACT CCCCGAAC<br>     BamHI | (SEQ ID NO:7) |
| 11.6 5'TT<u>GGATCC</u>TT ATCGGCC TTTCACCAGC CA<br>     BamHI | (SEQ ID NO:8) |

Alternatively, the small sizes of the signal peptide and GLP-1 moieties needed allow complete fusion genes to be prepared synthetically. DNA encoding the signal peptides of the LDL receptor (amino acid residues 1-21), preproglucagon (amino acid residues 1-20), or human growth hormone (amino acid residues 1-26) may be synthesized by known methods and ligated in vitro to similarly synthesized DNA encoding amino acids 7-37 or 7-36 of GLP-1 (followed immediately by a stop codon). The sequences necessary to design and synthesize these molecules are readily available in Genhank entries HUMLDLRO 1 (human LDL receptor), HUMGLUCG2 (human GLP-1 and glucagon sequences) and HUMGHCSA (human growth hormone). The ligated product may be inserted into a suitable mammalian expression vector for use in human fibroblasts. Plasmid pMSG (Pharmacia LKB Biotechnology, Piscataway, N.J.) is suitable for this purpose, having 5' and 3' untranslated sequences, a splice site, a polyA addition site, and an enhancer and promoter for use in human skin fibroblasts. Alternatively, the ligated product may be synthesized with an appropriate 5'-untranslated sequence and inserted into plasmid pX1 described above.

A second insulinotropic GLP-1 derivative, GLP-1(7-36), can be expressed by substituting oligonucleotide 11.6 for oligonucleotide 11.2 described above. All subsequent cloning operations described above for construction of pXGLP1 are described in Example 10 and blood samples are taken to monitor serum human GLP-1(7-37) levels.

In vivo activity is monitored in fasting animals by determining the insulinogenic index after intraperitoneal injection of glucose (1 mg glucose per gram of body weight). Typically, implanted and non-implanted groups of 32 mice are fasted overnight, and 28 are injected with glucose. After injection, the 28 mice are arbitrarily assigned to seven groups of four, and blood sampling (for serum glucose and insulin) is performed on each group at 5, 10, 20, 30, 45, 60, or 90 minutes post-injection, with the non-glucose injected group serving as a fasting control. Increases in the postinjection insulinogenic index (the ration of insulin to glucose in the blood) in animals receiving GLP-1(7-37) expressing cells over non-implanted animals provides in vivo support for the insulinotropic activity of the expressed peptide.

Equivalents

Those skilled in the art will recognize, or be able to ascertain using not more than routine experimentation, many equivalents to the specific embodiments of the invention described herein. Such equivalents are intended to be encompassed by the following claims.

The invention claimed is:

1. A transfected primary or secondary cell of vertebrate origin having stably integrated into its genome:
   a) exogenous DNA which encodes erythropoietin and
   b) DNA sequences, sufficient for expression of the exogenous DNA in the transfected primary or secondary cell, the primary or secondary cell capable of expressing erythropoietin.

2. The transfected primary or secondary cell of vertebrate origin of claim 1 selected from the group consisting of: transfected fibroblasts, transfected keratinocytes, transfected epithelial cells, transfected endothelial cells, transfected glial cells, transfected neural cells, transfected formed elements of the blood, transfected muscle cells, transfected hepatocytes, and transfected precursors thereof.

3. The transfected primary or secondary cell of claim 2 which is of mammalian origin.

4. The transfected primary or secondary cell of claim 3 selected from the group consisting of: transfected primary human cells, transfected secondary human cells, transfected primary rabbit cells and transfected secondary rabbit cells.

5. The transfected primary or secondary cell of vertebrate origin of claim 1 which additionally includes DNA encoding a selectable marker.

6. The transfected primary or secondary cell of claim 5 selected from the group consisting of: transfected fibroblasts, transfected keratinocytes, transfected epithelial cells, transfected endothelial cells, transfected glial cells, transfected neural cells, transfected formed elements of the blood, transfected muscle cells, transfected hepatocytes, and transfected precursors thereof.

7. The transfected primary or secondary cell of claim 6 which is of mammalian origin.

8. The transfected primary or secondary cell of claim 7 selected from the group consisting of: transfected primary human cells, transfected secondary human cells, transfected primary rabbit cells, and transfected secondary rabbit cells.

9. The transfected primary or secondary cell of vertebrate origin of claim 1 selected from the group consisting of:
   a) transfected primary or secondary cells which, in their untransfected state, do not make or contain erythropoietin;
   b) transfected primary or secondary cells which, in their untransfected state, make or contain erythropoietin in abnormally low amounts or in defective form; and
   c) transfected primary or secondary cells which, in their untransfected form, make or contain erythropoietin in physiologically normal amounts.

10. A primary or secondary cell of vertebrate origin transfected with:
    a) exogenous DNA which encodes erythropoietin; and
    b) DNA sequences, sufficient for expression of the exogenous DNA in the primary or secondary cell, the sequences of (a) and (b) present in the cell in an episome.

11. The primary or secondary cell of vertebrate origin of claim 10 selected from the group consisting of: fibroblasts, keratinocytes, epithelial cells, endothelial cells, glial cells, neural cells, formed elements of the blood, muscle cells, hepatocytes, and precursors thereof.

12. The primary or secondary cell of claim 11 which is of mammalian origin.

13. The primary or secondary cell of claim 12 selected from the group consisting of: primary human cells, secondary human cells, primary rabbit cells, and secondary rabbit cells.

* * * * *

UNITED STATES PATENT AND TRADEMARK OFFICE
CERTIFICATE OF CORRECTION

PATENT NO. : 7,410,799 B2
APPLICATION NO. : 10/885899
DATED : August 12, 2008
INVENTOR(S) : Selden et al.

It is certified that error appears in the above-identified patent and that said Letters Patent is hereby corrected as shown below:

Under column 5 line 35, replace "(PMMT1)" with --(pMMT1)--.

Under column 6 line 65, replace "A. D." with --A.D.--.

Under column 12 line 35, replace "GLP-1 (7-truncated" with --GLP-1 (7-34) and other truncated--.

Under column 16 line 13, replace "G418'" with --G418$^r$--.

Under column 19 line 29, replace "Hepo" with --hEPO--.

Under column 23 line 53, replace "HUMLDLRO 1" with --HUMLDLRO1--.

Signed and Sealed this

Third Day of February, 2009

JOHN DOLL
*Acting Director of the United States Patent and Trademark Office*

SEQUENCE LISTING

<160> NUMBER OF SEQ ID NOS: 8

<210> SEQ ID NO 1
<211> LENGTH: 31
<212> TYPE: DNA
<213> ORGANISM: Homo sapiens

<400> SEQUENCE: 1
cccatattac gtttgctcag cttggtgctt g                                    31

<210> SEQ ID NO 2
<211> LENGTH: 30
<212> TYPE: DNA
<213> ORGANISM: Homo sapiens

<400> SEQUENCE: 2
cccatattac tcaagttggc cctgtgacat                                      30

<210> SEQ ID NO 3
<211> LENGTH: 34
<212> TYPE: DNA
<213> ORGANISM: Homo sapiens

<400> SEQUENCE: 3
cccatattac catgctgaag ggacctttac cagt                                 34

<210> SEQ ID NO 4
<211> LENGTH: 42
<212> TYPE: DNA
<213> ORGANISM: Homo sapiens

<400> SEQUENCE: 4
cccatattac ttggatcctt atcctcggcc tttcaccagc ca                        42

<210> SEQ ID NO 5
<211> LENGTH: 54
<212> TYPE: DNA
<213> ORGANISM: Homo sapiens

<400> SEQUENCE: 5
cccatattac ggcttcaaga gggcagtgcc catgctgaag ggacctttac cagt           54

<210> SEQ ID NO 6
<211> LENGTH: 54
<212> TYPE: DNA
<213> ORGANISM: Homo sapiens

<400> SEQUENCE: 6
cccatattac actggtaaag gtcccttcag catgggcact gccctcttga agcc           54

<210> SEQ ID NO 7
<211> LENGTH: 38
<212> TYPE: DNA
<213> ORGANISM: Homo sapiens

<400> SEQUENCE: 7
cccatattac aaggatccca aggcccaact ccccgaac                             38

<210> SEQ ID NO 8
<211> LENGTH: 39
<212> TYPE: DNA
<213> ORGANISM: Homo sapiens

```
<400> SEQUENCE: 8
cccatattac ttggatcctt atcggccttt caccagcca                              39
```